US009019503B2

(12) United States Patent
Ouyang et al.

(10) Patent No.: US 9,019,503 B2
(45) Date of Patent: Apr. 28, 2015

(54) MEMS MICRODISPLAY OPTICAL IMAGING AND SENSOR SYSTEMS FOR UNDERWATER AND OTHER SCATTERING ENVIRONMENTS

(71) Applicants: Bing Ouyang, Vero Beach, FL (US); Fraser Dalgleish, Vero Beach, FL (US); Anni Dalgleish, Vero Beach, FL (US)

(72) Inventors: Bing Ouyang, Vero Beach, FL (US); Fraser Dalgleish, Vero Beach, FL (US); Anni Dalgleish, Vero Beach, FL (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/021,822

(22) Filed: Sep. 9, 2013

(65) Prior Publication Data

US 2014/0204385 A1 Jul. 24, 2014

Related U.S. Application Data

(63) Continuation-in-part of application No. 13/089,715, filed on Apr. 19, 2011, now Pat. No. 8,917,395.

(60) Provisional application No. 61/325,449, filed on Apr. 19, 2010.

(51) Int. Cl.
*G01N 21/00* (2006.01)
*G01N 21/55* (2014.01)
*G01N 21/47* (2006.01)
*G01N 21/17* (2006.01)

(52) U.S. Cl.
CPC ............... *G01N 21/55* (2013.01); *G01N 21/47* (2013.01); *G01N 2021/1793* (2013.01); *G01N 2201/0675* (2013.01)

(58) Field of Classification Search
CPC .................................................... G01N 21/553
See application file for complete search history.

(56) References Cited

U.S. PATENT DOCUMENTS

| | | | |
|---|---|---|---|
| 3,775,735 | A | 11/1973 | Funk et al. |
| 4,088,898 | A | 5/1978 | Stitch |
| 4,707,128 | A | 11/1987 | Coles |
| 5,046,259 | A | 9/1991 | Tusting |
| 5,418,608 | A | 5/1995 | Caimi et al. |
| 6,072,903 | A | 6/2000 | Maki et al. |
| 6,723,975 | B2 | 4/2004 | Saccomanno |

(Continued)

OTHER PUBLICATIONS

Baraniuk, "Compressive sensing", IEEE Signal Processing Magazine (2007) 24: 118-121.

(Continued)

*Primary Examiner* — Michael P Stafira

(57) ABSTRACT

A sensing system is provided that includes a transmitter assembly with a light source and a microdisplay device, wherein the transmitter assembly defines an optical beam transmission path to provide illumination of a substantially one-dimensional (1D) region of a target area, the microdisplay device comprising a plurality of controllable elements for causing the illumination to be a substantially 1D pattern of light along the 1D region. The system further includes a receiver assembly for defining a return optical signal transmission path from the 1D region and collecting return optical signals from the 1D region. The system also includes a processing component for generating sensor information associated with the 1D region by processing the return optical signals from the 1D region with return optical signals from adjacent 1D regions using a distributed compressive sensing (DCS) technique.

20 Claims, 23 Drawing Sheets

(56) References Cited

U.S. PATENT DOCUMENTS

| | | | |
|---|---|---|---|
| 7,355,648 B1* | 4/2008 | Braun et al. | 348/370 |
| 7,609,875 B2 | 10/2009 | Liu et al. | |
| 2006/0066944 A1 | 3/2006 | Okugawa | |
| 2008/0218821 A1 | 9/2008 | Dalgliesh et al. | |

OTHER PUBLICATIONS

Baron et al., "Distributed compressed sensing", Rice University, Department Electrical and Computer Engineering Technical Report (2006) TREE-0612.

Candes, "Compressive sampling", Proc Int Cong Mathematicians (2006) 3: 1433-1452.

Candes et al., "Near optimal signal recovery from random projections: Universal encoding strategies", IEEE Trans Inform Theory (2006) 52: 5406-5425.

Candes et al., "Robust signal recovery from incomplete observations", Proc ICIP (2006): 1281-1284.

Candes et al., "Sparsity and incoherence in compressive sampling", Inverse Problems (2007) 23: 969-985.

Candes et al., "Stable signal recovery from incomplete and inaccurate measurements", Comm Pure Appl Math (2006) 59(8): 1207-1223.

Carron, "Nuit Blanche", Blog. Retrieved on Oct. 10, 2013, from http://nuit-blanche.blogspot.com/2008/06/cs-another-single-pixel-camera-atrice.html (3 pages).

Chen et al., "Atomic decomposition by basis pursuit", SIAM J Science Comp (1999) 20: 33-61.

Dalgliesh et al., "Improved LLS imaging performance in scattering-dominant waters", SPIE (2009) 7317: 73170E.

Dalgliesh et al., "Synchronous laser line scanners for undersea imaging.applications", Ch. 16. Handbook of Optical and Laser Scanning. CRC Press. (2011): 731-750.

De Haan et al., "Deinterlacing—An Overview", Proc of the IEEE (1998) 86(9): 1839-1857.

Do et al., "Distributed compressed video sensing", Proc IEEE Int Conf on Image Processing (2009): 1393-1396.

Donoho, "Compressed sensing", IEEE Trans Inform Theory (2006) 52(4): 1289-1306.

Doyle et al., "Progressive scan conversion using edge information", Signal Processing of HDTV II (1990)711-721.

Duarte et al., "Single-pixel imaging via compressive sensing", IEEE Signal Processing Magazine (2008) 25: 83-91.

Dudley et al., "Emerging digital micromirror device (DMD) applications", Proc of SPIE (2003) 4985: 14-25.

Farouk, "MPEG bit rate improvement using adaptive GOP", International Journal of Circuits, Systems and Signal Processing (2007) 1: 8-11.

Gan et al., "Fast compressive imaging using scrambled block Hadamard ensemble", Proc EUSIPCO (2008) (5 pages).

Jaffe, "Performance bounds on synchronous laser line scan systems", Optical Society of America, Optics Express (2005) 13(3): 738-748.

Jaffe et al., "Underwater optical imaging: status and prospects", Oceanography (2001) 14(3): 64-76.

Kang et al., "Distributed compressive video sensing", Proc IEEE Int Conf on Acoustics, Speech and Signal Processing (2009): 1169-1172.

Kulp et al., "Development and testing of a synchronous-scanning underwater imaging system capable of rapid two-dimensional frame imaging", Applied Optics (1993) 32(19): 3520-3532.

Lukin, "High-quality spatial interpolation of interlaced video", Proc of Graphicon (2008): 114-117.

Mullen et al., "Modulated laser line scanner for enhanced underwater imaging", Proceedings of SPIE (1999) 3761: 2-9.

Ouyang et al., "Underwater laser serial imaging using compressive sensing and digital mirror device", SPIE (2011) 8037: 803707.

Raginsky et al., "Performance bounds for expander-based compressed sensing in the presence of Poisson noise", Proc Asilomar Conference on Signals, Systems, & Computers (2009) (15 pages).

Tropp et al., "Random filters for compressive sampling and reconstruction", Proc ICASSP (2006): 872-875.

\* cited by examiner

*image quality varies with measurement rate*

MEMS MICRODISPLAY OPTICAL IMAGING AND SENSOR SYSTEMS FOR UNDERWATER AND OTHER SCATTERING ENVIRONMENTS

RELATED APPLICATIONS

This application is a continuation-in-part of U.S. non-Provisional patent application Ser. No. 13/089,715, filed 19 Apr. 2011, which claims priority to U.S. Provisional Patent Application Ser. No. 61/325,449, filed 19 Apr. 2010, the contents of both of which are incorporated herein by reference in their entirety.

STATEMENT REGARDING FEDERALLY SPONSORED DEVELOPMENT

Development of this invention was supported in part by Award No. N00014-09-1-0714, awarded by the United States Office of Naval Research. Accordingly, the United States Government may have certain rights in this invention.

FIELD OF THE INVENTION

This application relates generally to imaging systems and methods and, in particular, has application in characterization of surfaces, e.g., reflectance profiles, from remote positions wherein visibility through a medium may be range limited or otherwise obscured by, for example, light scattering effects or other phenomena which can limit transmission of optical data. This application also relates to measurement of light scattering characteristics in a medium.

BACKGROUND OF THE INVENTION

In both terrestrial and submarine environments there are situations in which the transmission of imaging information through the field of view is limited rendering it difficult to characterize surfaces with conventional imaging system components such as, for example, a CCD-based imaging device and a divergent illumination source. One common limiting factor is the presence of a large number of suspended particles in the field of view. Not only does this result in significant back scattering of light, but it also contributes to transmission loss of imaging detail. Typically, when the predominant component of energy received by the imaging device is attributable to scattered light, the signal-to-noise ratio is too low to provide useful information.

Several designs and configurations have emerged for underwater imaging applications at varied ranges. Conventional camera systems having an adjacent broad spectrum light source are useful for imaging surfaces at distances of one to two attenuation lengths. An attenuation length is the distance light must travel to be reduced to 1/e of its original intensity. The attenuation length is typically 20 to 30 m in clear water. It has been found that at distances of about three attenuation lengths, acceptable imaging can be provided by spatially separating the light source from the camera, e.g., using a flood light to illuminate the target region.

At imaging distances greater than three attenuation lengths, laser-based systems are more effective. These extended range imagers are generally of two classes: the synchronous laser line scanner (LLS) and the range gated scanner. See Jaffe,]; S. et al. "Underwater Optical Imaging: Status and Prospects", Oceanography, Vol. 14, No. 3 pp. 66-76 (2001). See, also, U.S. Pat. Nos. 4,707,128 and 5,418,608 each of which is incorporated herein by reference. These types of imaging systems can provide acceptable real-time image data in the range of 3 to 7 attenuation lengths. Such imagers have been under continued development for use in Autonomous Underwater Vehicles (AUVs) and Remotely Operated Underwater Vehicles (ROVs) to provide surface information needed for navigation as well as for characterizing the sea floor for varied activities including military missions and construction of oil and gas infrastructures.

Synchronous LLS systems provide scanning capability with a continuous wave (CW) laser source. Based on results of controlled experimentation and analytical modeling, synchronous scanners have been found capable of operation at maximum distances of about 5 to 6 attenuation lengths. Further improvement in imaging range would benefit undersea operations by allowing increased vehicle speed and maneuverability and improved image resolution at greater distances from target regions. By way of example, in the exploration of unknown or dynamic environments, rapid topographical seabed variations can occur at rates greater than the vertical axis performance of the AUV. It is therefore necessary to distance the vehicle at a sufficient range above the seabed to avoid potentially catastrophic collisions. Optimal underwater optical scanner designs must consider this AUV trajectory.

The ability to more rapidly produce higher resolution images of targets and survey sites from greater distances will enable a more extensive and diverse set of applications for underwater vehicles. Depending on the size and complexity of surfaces in the target region, optical sensing may be the only effective means for characterizing features.

It has also been shown by both simulation and experimentation that the class of range-gated imagers i.e., those imagers utilizing a pulsed laser source, may be capable of adequate underwater performance for imaging target regions at distances up to seven attenuation lengths. These systems minimize introduction of energy due to scattered light with gating electronics. Although these imagers ultimately become power (or photon) limited due to the exponential decay rate of light traveling through the water, they can be more compact than CW LLS systems because a spatial offset between the source and receiver is not required to reject scattered light.

Summarily, both classes of extended range underwater imagers ultimately are limited in range by the cumulative effects of forward scattering events and divergence of the illumination, particularly as the reflected signal travels from the target region to the imaging system. Scattering causes losses in contrast, resolution and signal to noise ratio (SNR). These losses are particularly problematic at and near the range limit of operation.

Relatively small depth of field (DOF) has also been a disadvantage in prior LLS system designs. This is particularly problematic when imaging in a dynamic undersea environment in which there is significant variation in optical transmission properties or in sea bed surface features or in which there is significant variation in platform altitude or attitude. With a small DOF each of these factors can lead to unacceptable degradation in image quality or complete signal loss. The DOF is a function of the source-receiver separation distance, the optical path length to and from the target, beam divergence and the acceptance angle of the receiver. The receiving aperture of the LLS system may be widened to improve DOF. Alternately, a fine adjustment of the optical focus may be slaved in accord with an on-board altimeter.

Range-gated imagers have also had inherent disadvantages in addition to limitations in imaging distance. For example, variations in distance between the system and a target surface result in a change in the required delay time of the gating function used to selectively acquire photons returning from the target.

Based on the foregoing it is apparent that both classes of extended range imagers have performance limitations restricting usefulness in a variety of potential applications including, for example, smoke-filled environments, fog, adverse weather conditions and underwater imaging. In addition, the size, weight and power requirements are also extremely important when designing an imager for portable or mobile deployment in any of the afore-described environments.

The optical resolution achievable with a LLS system is dependent on the laser beam diameter at the reflecting surface in the target region, and is also dependent upon the precision with which the receiver can resolve intensity information from the return signal as a function of the scan angle. Minimizing the instantaneous field of view (IFOV), e.g., by minimizing the spot size at the target, reduces the scattering volume, which reduction can improve the signal-to-noise ratio. That is, the imaging range of the system can be improved by reducing the size of the scattering volume. Reducing the IFOV reduces the target area per pixel, commonly measured in $cm^2$ per pixel and, theoretically, improves image resolution. This is particularly desirable when imaging target surfaces having a high spatial frequency, as the combined effects of forward scattering and blurring, due to the limited DOF, further limit the achievable resolution.

The '821 patent describes a synchronized laser beam scanning system in which the scanning architecture is built around a single six faceted polygonal scan mirror. The system provides a very narrow instantaneous field of view (IFOV) at the receiver channel which is optically coincident with the outgoing laser pulse throughout the entire scan angle for a fixed stand-off distance. Using two symmetrical steering mirror assemblies, one for the outgoing beam and one for the returning signal, optical synchronization can be maintained as the stand-off distance is adjusted. The symmetry of the source and receiver channels about the center axis of the polygon also significantly reduces the necessary size of the detector photocathode area required to complete a full scan through a wide angle. Polygonal mirror systems are widely used in other laser scanning systems. See, for example, U.S. Pat. No. 6,723,975. However, provision of mechanically rotatable polygonal mirrors in scanners poses a significant addition to the system size and cost and may affect reliability. Efforts to build small, more compact laser line scanners of this type are subject to limitations because of the mechanical nature of the rotating mirror systems. Another intrinsic limitation of the raster scanning based techniques such as the LLS system is that in order to maintain the image resolution with increased platform speed, higher laser repetition rate will be required. This in turn affects the system cost and complexity (i.e., noise mitigation of wider bandwidth electronics).

U.S. Pat. No. 7,609,875, referred to herein as the '875 patent, also incorporated herein by reference, discloses a Micro-Electro-Mechanical Systems (MEMS) based laser scanning system having a MEMS mirror which can oscillate in two independent directions. A high speed modulated or pulsed laser beam is transmitted through a fiber collimator and is then radiated toward the MEMS mirror which reflects the beam through a fixed optical path, consisting of a beam splitter, a lens and a static mirror, to the target. Light reflected from the target traverses the same fixed optical path in a reverse direction before entering the receiver. The system as disclosed in the '875 patent does not include any measures to mitigate signal impairment due to volume backscattering or other light scattering phenomena.

SUMMARY OF THE INVENTION

The various embodiments of the invention are directed to imaging systems and methods for imaging from remote positions wherein visibility through a medium may be range limited or otherwise obscured by, for example, light scattering effects or other phenomena which can limit transmission of optical data.

In a first embodiment, there is provided a sensing system. The system includes a transmitter assembly, comprising a light source and a microdisplay device, defining an optical beam transmission path to provide illumination of a substantially one-dimensional (1D) region of a target area, the microdisplay device comprising a plurality of controllable elements for causing the illumination to be a substantially 1D pattern of light along the 1D region. The system also includes a receiver assembly for defining a return optical signal transmission path from the 1D region and collecting return optical signals from the 1D region. The system further includes a processing component for generating sensor information associated with the 1D region by processing the return optical signals from the 1D region with return optical signals from adjacent 1D regions using a distributed compressive sensing (DCS) technique. In the system, the sensor information can be image information.

In the system, the processing component can include a processor and a computer-readable medium comprising a plurality of instructions for causing the processor to perform various steps. These steps can include identifying at least one aperture section in the target area that includes the 1D region and at least a portion of the adjacent 1D regions to yield aperture 1D regions for each at least one aperture section, computing a solution for aperture 1D regions using the DCS technique for each at least one aperture section, and combining the solution of the 1D region from each at least one aperture section to produce the sensor information for the 1D region.

In the system, the return optical signals from the 1D region and the return optical signals from the adjacent 1D regions can be associated with a sequence of adjacent positions for the sensing system over the target.

In the system, measurement matrices for the DCS technique can be generated using a radiative transfer model based on at least one of environmental conditions and a configuration of the platform.

In a second embodiment, a method is provided. The method includes obtaining data associated with a plurality of return optical signals generated for a series of substantially one-dimensional (1D) regions of a target area, each of the plurality of return optical signals generated by illuminating each of the series of 1D regions using a substantially 1D pattern if light along a width of the 1D regions. The method also includes identifying at least one aperture section for the target area that includes at least a portion of the 1D regions to yield aperture 1D regions for each at least one aperture section, computing a solution for the aperture 1D regions using a distributed compressive sensing (DCS) technique for each at least one aperture section, and combining the solutions from each at least one aperture section to produce the sensor information for each of the 1D regions, In the method, the obtaining can include receiving measurement data corresponding to the return optical signals for each of the 1D regions and assembling a measurement matrices for each of the 1D regions based at least on the measurement data.

In the method, the measurement matrices can be based on a model accounting for at least environmental conditions during collection of the measurement data and a configuration of a transmitter assembly for providing the illumination and the receiver assembly for the collecting of the return optical signals.

In the method, the obtaining can further include directing light from a light source on a platform to the series of 1D regions using a microdisplay device at the platform to generate the return optical signals and collecting the return optical signals using a receiver at the platform, wherein the microdisplay device includes a plurality of controllable elements, and wherein the directing includes adjusting the plurality of controllable elements to cause the light to be reflected towards each of the series of 1D regions as the 1D pattern of light.

The obtaining can further include collecting one or more sets of measurement data for each of the series of 1D regions, wherein a number of the sets of measurement data for each of the series of 1D regions is selected based on at least one of a speed of the platform, a desired refresh rate for the sensor information, and an expected resolution of the sensor information.

In the method, the computing can be performed using one of a DCS-JSM1 algorithm or a GDCS algorithm.

In a third embodiment of the invention, there is provided a method for operating a sensing system on a moving platform that comprises a transmitter assembly for transmitting an optical beam transmission path to provide illumination of each of a series of adjacent substantially one-dimensional (1D) regions of a target area using substantially 1D patterns of light and a receiver assembly for defining a return optical signal transmission path from the series of 1D regions and collecting return optical signals from the series of 1D regions. The method can include initializing the sensing system to set a first number of measurements for each of the series of 1D regions, a second number of the series of 1D regions defining an aperture section of the target area, and a configuration of measurement matrices for the series of 1D regions, and performing a reconstruction process to assemble an image of the target area.

The reconstruction process includes generating the measurements for a one of the series of 1D regions, updating a first-in, first-out (FIFO) buffer with an entry comprising the measurements and the measurement matrices corresponding to the one of the series of 1D regions, determining whether the FIFO buffer includes a number of entries equal to the second number, and, in response to the FIFO buffer including a number of entries equal to the second number, computing a solution for the series of 1D regions in the FIFO buffer using a distributed compressive sensing (DCS) technique in response to the FIFO buffer including a number of entries less that the second number repeating the process.

The method can further include detecting that a one of the series of 1D regions is no longer in the FIFO buffer and combining the solution for the one of the series of 1D regions from each time the reconstruction process is performed.

In the method, the initializing can include calculating the first number based on at least one of the speed of the platform, a refresh rate of the 1D patterns, and an expected resolution. The initializing can further include calculating the second number based at least on characteristics of a medium associated with the optical beam transmission path and the return optical signal transmission path.

In the method, the measurement matrices can be generated using a radiative transfer model based on at least one of environmental conditions and a configuration of the platform.

In the method, the reconstruction process can further include adjusting the second number based on a difference in the data between the series of 1D regions.

Further, in the method, the computing can be performed using one of a DCS-JSM1 algorithm or a GDCS algorithm.

BRIEF DESCRIPTION OF THE DRAWINGS

Features of the invention will be best understood when the following detailed description is read in conjunction with the accompanying drawings wherein:

FIGS. 22A-22C schematically illustrates a compressive line sensing imager system according to the invention;

Figure 1:
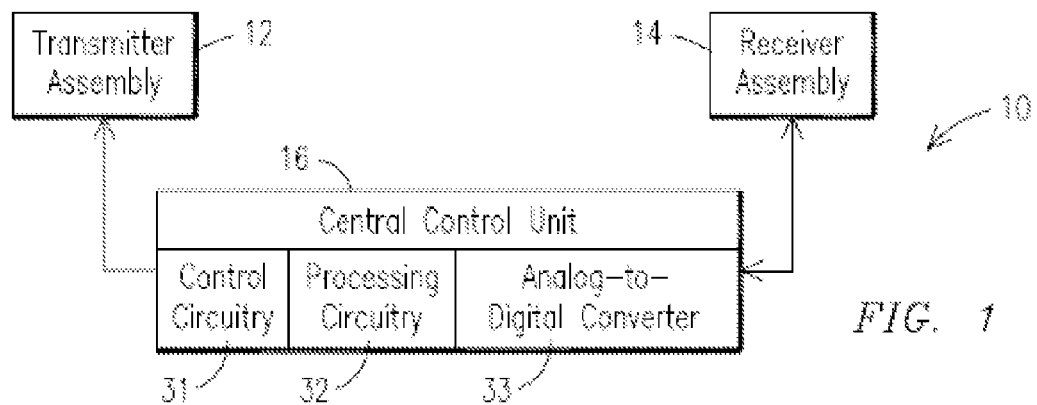
FIG. 1 is a simplified block diagram illustrating an imaging system according to an embodiment of the invention.

Like reference numbers are used throughout the figures to denote like components. Numerous components are illustrated schematically, it being understood that various details, connections and components of an apparent nature are not shown in order to emphasize features of the invention. Various features shown in the figures are not shown to scale in order to emphasize features of the invention.

DETAILED DESCRIPTION OF THE INVENTION

Before describing in detail the particular methods and apparatuses related to embodiments of the invention, it is noted that the present invention resides primarily in a novel and non-obvious combination of components and process steps. So as not to obscure the disclosure with details that will be readily apparent to those skilled in the art, certain conventional components and steps have been omitted or presented with lesser detail, while the drawings and the specification describe in greater detail other elements and steps pertinent to understanding the invention. Further, the following embodiments do not define limits as to structure or method according to the invention, but only provide examples which include features that are permissive rather than mandatory and illustrative rather than exhaustive.

The embodiments described herein are based in part on concepts disclosed in US Patent Application Publication No. 20080218821, now incorporated herein by reference, titled "Method and Apparatus for Synchronous Laser Beam Scanning" and referred to herein as the '821 patent.

While not limited to such, the concepts and designs now described apply to imaging and sensor systems and are particularly useful in environments characterized by light scattering. Embodiments of the invention have application in systems such as flash LIDAR (Light Detector and Ranging) systems and LLS (laser line scanner) systems where sensing of light reflected from the target can be impaired by scattering and wherein use of adaptive sampling schemes are advantageous. Also the described approaches provide the potential of achieving desirable image resolution without requiring high repetition rate (i.e. costly) laser.

Imaging and sensor systems according to the invention are based, in part, on principles outlined in the '821 patent to maintain optical synchronization between transmitted and received signals and to minimize the receiver IFOV so that interference from volume backscattering can be minimized. According to one series of embodiments, a pair of microdisplay devices is used in lieu of a mechanically rotating polygonal mirror to achieve synchronization. As used herein, the term "microdisplay devices" refers to members of the family of microchips which can be electronically controlled to spatially modulate reflection of light signals, e.g., as commonly used to project an image on a screen or to illuminate a target region. Most microdisplay devices are fabricated with standard CMOS technology, rendering volume manufacture both reliable and economical. Among the variety of microdisplay devices, there are MEMS scanning mirrors, Digital Micromirror Devices (DMD's), Liquid Crystal on Silicon (LCOS) devices, High Temperature Poly-Silicon (HTPS) panel (also known as LCD panel) devices and Grating Light Valve devices etc. Since a variety of the microdisplay devices operate according to different mechanisms, different optical configurations may be required to incorporate these into imaging and scanning systems according to the invention, and a variety of system designs may be constructed according to the teachings provided herein.

It is suggested in the '821 patent that the receiver should provide a resolution of $1/1000$ radian. With arrays having elements on the order of 1920×1080, all of the aforementioned microdisplay devices are capable of providing at least this resolution. Therefore all these types of devices or a combination of them can be used to synchronize transmitter and receiver signals. In accord with embodiments of the invention, additional microdisplay devices may be cascaded and used additively to spatially modulate (e.g., transmit or block) light transmission along an optical path to thereby further minimize the receiver IFOV to any given precision.

One of the embodiments based on DMD's is a system which includes a first DMD positioned in a light transmission path and a second DMD positioned in a return signal (receiver) path. Such an example embodiment is now described with the understanding that this is exemplary of one implementation of the inventive concepts. Each DMD comprises a plurality of micro mirrors that can be individually controlled, e.g., turned on or turned off, to direct light toward or away from a receiving lens, to either allow illumination of a spatial location or allow receipt of light signals reflected from the spatial location. In principle a similar approach may be effected with other microdisplay devices. A MEMS scanning mirror can also be used to control transmission or receipt of signals from discrete spatial locations, and this may be effected in a sequential manner.

Figure 2:
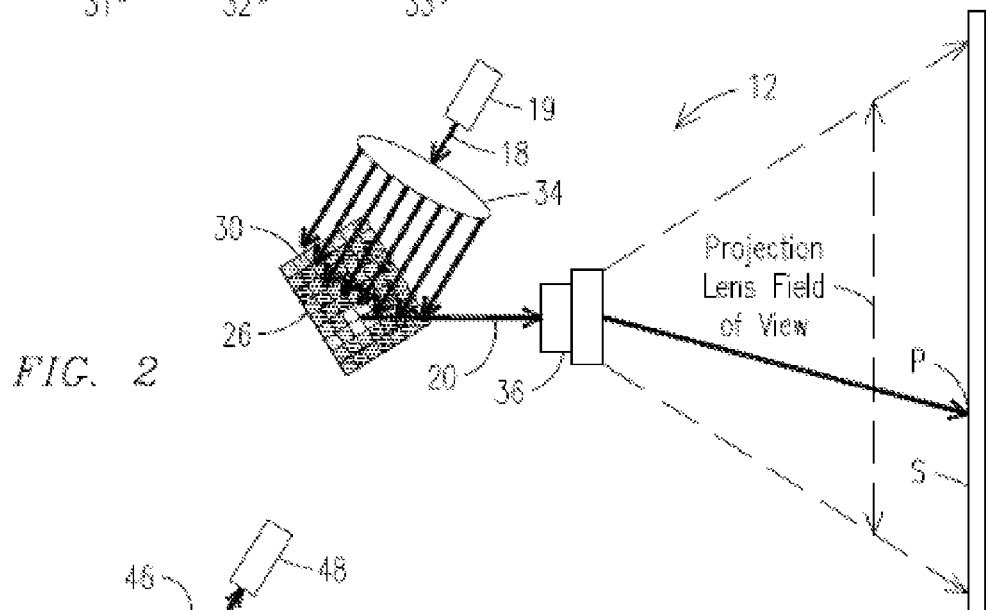
FIG. 2 is a schematic view of the transmitter assembly of the system shown in FIG. 1.

With reference to FIGS. 1-4, an imaging system 10 comprises a transmitter assembly 12 and a receiver assembly 14 operable under the control of a central control unit 16 as shown in the block diagram of FIG. 1. With reference to FIG. 2, the transmitter assembly 12 receives a light beam 18 generated by a laser source 19 which propagates along an outgoing optical beam transmission path 20 indicated by arrows in FIG. 2 to a target surface, S. The receiver assembly 14, shown in FIG. 3, receives a light signal 21 reflected from the target surface S which propagates along a return (receiving) optical signal transmission path 22 indicated in FIG. 3 by arrows. The transmitter assembly 12 includes a transmitter DMD 26 positioned in the outgoing beam transmission path 20. The receiver assembly 14 includes a receiver DMD 28 positioned in the return signal transmission path 22.

In this example and in other disclosed embodiments, each DMD is of a conventional design, comprising an array of mirror elements 30 arranged in rows and columns. Each mirror element can be individually selected to move from a blocking position to a transmit position. When in the blocking position a mirror element reflects none, or substantially none, of the received light along a defined transmission path. For example, when a mirror element 30 of the DMD 26 is not selected, it remains in the blocking position so that it reflects none, or substantially none, of the light beam along the outgoing optical beam transmission path 20. Similarly, when a mirror element 30 of the DMD 28 is not selected, it remains in the blocking position so that it reflects none, or substantially none, of the light signal 21, received by the receiver assembly 14 from the target surface, along the return signal transmission path 22.

In an initial state one or both of the DMDs 26, 28 may be in a non-transmitting off state wherein all of the mirror elements in the DMD array are in the blocking position, thereby preventing transmission through the optical paths 20, 22. As used herein the term transmit angle refers to predetermined angle at which each mirror element 24 in a DMD can be selectively placed in order to effect reflection of light in and along an optical transmission path. When a DMD is in the off state none of the mirror elements are selected to be placed at the transmit angle. When one or more mirror elements are selected to be positioned at the transmit angle, they are referred to as being in a transmit mode, while the other mirror elements are referred to as being in a blocking mode because they are not configured to reflect light along the optical transmission path. As used herein, the term pointing angle refers to the angle of the outgoing light beam relative to the center of the projection axis. In the figures individual mirror elements 30 which are in the blocking mode are illustrated with shading while individual elements 30 which are in the transmit mode are illustrated without shading.

The central control unit 16 comprises control circuitry 31, processing circuitry 32 and an analog-to-digital converter 33. The processing circuitry 32 effects data collection and post processing for image generation and enhancement. The control analog-to-digital converter 33 receives an analog output from a photomultiplier detector in the receiver assembly 14.

The control circuitry 31 of the central control unit 16 controls movement of the mirror elements of the DMD's in the system 10. Specifically, the control unit defines a pointing angle of the light beam 18 with respect to the target surface S by placing one or more of the elements 30 of the DMD 26 in a transmit mode so that, at any given time, only selected mirror elements in the DMD 26 are placed in the transmit mode, i.e., to reflect a portion of the light beam along the optical path 20. With this capability the size and the pointing direction of the light beam are controllable. By way of example, a row-by-row and element-by-element selection of adjacent elements 30 can create a raster-like scan pattern along the target surface S. In one embodiment, such a scan sequentially and individually places each element 30 in the transmit mode while all other mirror elements are in the blocking mode. Alternately, the control unit may define groups of adjoining elements 30 and sequentially place groups adjoining or overlapping groups elements 30 in the transmit mode. When each group of elements 30 is selected to be in the transmit mode all other mirror elements are in the blocking mode.

A scan which sequentially and individually places individual elements 30 in the transmit mode is a serial selection of individual elements which sequentially progresses from a first element in a first row to an adjacent element in the same row, then sequentially performing the same serial progression in each other row where row selection progresses serially from the first row to an adjacent row so that the progression moves element by element from the first row to the last row.

When the control unit defines a sequence of segments, each comprising multiple adjoining mirror elements 30, e.g., based on overlapping groups of adjoining elements 30, the beam throughput can be increased. For example, a first segment may comprise four elements 30, where two of the elements are in one row and two of the elements are in an adjacent row such that each element is adjacent two other elements. A second segment in the sequence may comprise two of the same elements of the first segment, but which are in different rows, and two new elements which each are in different rows from one another but next to one of the two elements which were also in the first segment. Generally, as used herein, the term segment refers to one element 30 or a group of adjacent elements 30 which are simultaneously placed in the transmit mode to effect propagation of a light beam or a light signal along a transmission path. For the DMD 26 each segment may be one in a sequence of segments that create a beam scan with, for example, the light beam 18.

Prior to placing each segment of mirrors of the DMD 26 in the transmit mode, the control unit 16 computes the corresponding IFOV of the receiver assembly 14 for that particular segment of mirrors based on (i) the selected size of the light beam transmitted to the target surface S (i.e., determined by the number of adjoining mirror elements placed in the transmit mode), and (ii) the pointing angle of the light beam reflected by the DMD 26 (i.e., an angle which varies based on the location of the selected element(s) in a segment).

Figure 3:
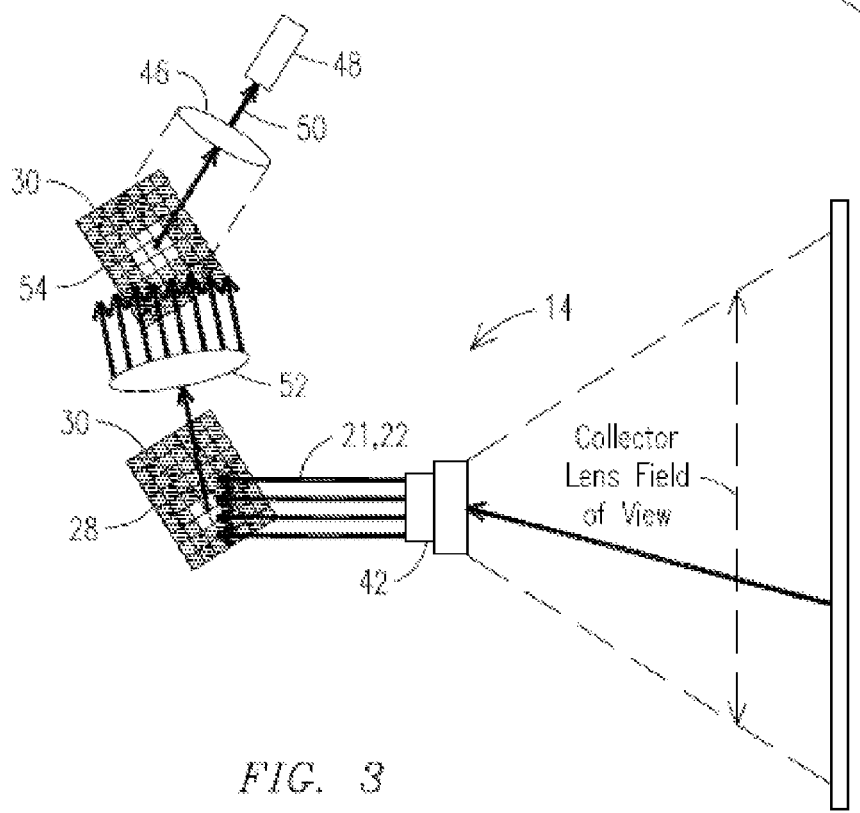
FIG. 3 is a schematic view of the receiver assembly of the system shown in FIG. 1.
Figure 4:
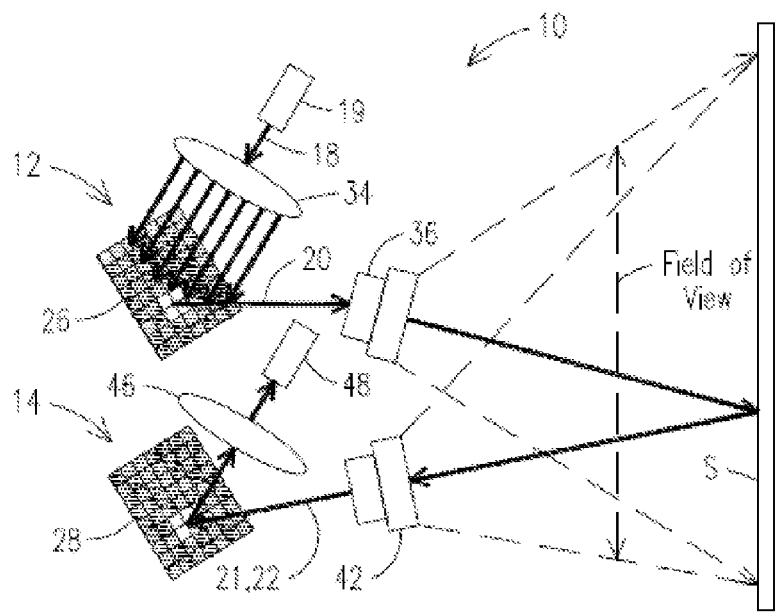
FIG. 4 is a schematic view of showing both the transmitter assembly and receiver assembly and associated optical transmission paths.

Also, with respect to each segment in the sequence of segments defined in the DMD 26, (i.e., the segments to be placed in the transmit mode), the control unit 16 identifies and selects a set of mirror elements 30 of the DMD 28 which elements form a segment in the receiver DMD 28 corresponding to the selected segment. The mirror elements in each identified segment are selected such that the effective field of view of the receiver assembly 14 is adjusted with the DMD 28 to correspond to the computed IFOV. In the illustration of FIGS. 2 and 3 the segments of elements shown as selected to be in the transmit mode for both the transmit assembly 12 and the receiver assembly 14 are shown to be the same, i.e., shown to cover the same areas of the DMDs, but this is only an example embodiment and different segments may be defined for each DMD.

As the control unit 16 places each segment, e.g., segment xx, of the DMD 26 in the transmit mode it also places the corresponding segment, e.g., segment yy, of the DMD 28 in the transmit mode to provide a complete optical path wherein the receiver assembly 14 has a time varying, e.g., programmable, field of view based on the computed IFOV.

The control unit 16 may also re-define the size of the selected segment of the DMD 28, i.e., to include more or fewer mirror elements 30, to expand or further limit the IFOV of the receiver. The control unit also performs numerous tasks common to image processing, including operation of the A/D Converter which receives signal information from the receiver assembly (e.g., via a photomultiplier tube) to record the return signal strength. Real-time and automated image adjustment becomes available because the field of view of the receiver assembly 14 is programmable in accord with selection of mirror elements of a DMD device. In addition, the control unit 16 can perform post processing such as filtering to reduce image noise and enhance image contrast to further enhance the signal to noise ratio (SNR). In the illustrated examples the control unit also provides display and image control via drivers and image enhancing software.

The transmitter assembly 12 further comprises a laser beam expander 34 and a projection lens 36 for imaging along the target surface. The transmission path 20 extends from the laser source 19 through the beam expander 34 to the DMD 26 such that the expander illuminates the surface 36 of the DMD which faces the expander with the light beam 18. All of the reflective surfaces of the mirror elements 30 receive a portion of the light beam 18. As discussed above, with a sequence of segments of mirror elements placed in the transmit mode by the control unit 16, portions of the beam 18 are sequentially reflected from the surface 36 by segments of mirror elements 30 which receive the beam so that the transmission path 20 extends from the reflective surface 36 of the DMD 26, through the projection lens 36 and to the target surface S. Accordingly the surface S is illuminated by the light beam 18.

The central control unit turns on a selected segment of the mirror elements 30 (e.g., a single mirror element, a row of mirror elements or some predetermined or randomly generated pattern of elements) of the DMD 26 so that mirror elements in the selected segment transition from the blocking mode to a preset transmit angle for the transmit mode, thereby illuminating a portion of a target surface S. As shown in FIG. 2, the projection lens 36 transmits a portion of the light beam 18 from a selected segment, e.g., segment 30T, at a predetermined pointing angle to illuminate a portion P of the target surface S. In this context the pointing angle refers to the angle of the outgoing light beam relative to the optical axis of the projection lens 36.

By way of example, it is to be understood that if each segment of mirror elements is a horizontal row of mirror elements in the transmitter DMD 26 then, by sequentially selecting adjacent elements in adjacent horizontal rows of the DMD 26, the mirror elements 30 are used to serially transmit full lines of laser light, and the transmitter assembly performs a line scan sweep along the target surface S commensurate with the projection lens field of view.

With reference to FIG. 3, embodiments of the receiver assembly 14 include a lens 42 functioning as a 'bucket' collector for collecting and focusing photons emanating from the target surface S on to the mirror elements 30 of the receiver DMD 28. The lens 42 may be a single plano-convex lens. The receiver assembly also includes a focusing lens 46 and a photomultiplier tube 48 having a photocathode 50. The focusing lens 46 condenses the light signal 21 on to the photocathode 50. The receiver assembly may optionally include, as shown in FIG. 3, an additional magnifying lens 52 and a reshaping DMD 54.

As the transmitter assembly 12 performs a scan along the target surface S, the receiver assembly 14 collects and focuses photons emanating from the target surface on to the mirror elements 30 of the DMD 28. A feature of the example embodiments is that unwanted light, (i.e., light which has either been scattered with the medium or scattered during propagation along the transmission path and reflected from an adjacent target region) can be eliminated at the receiver DMD 28. Elimination is effected by programming the receiver DMD 28 with the control unit 16 to effectively reduce the field of view of the receiver assembly 14. As described above, each time a segment of elements 30 of the transmit DMD 26 is placed in the transmit mode, only a segment of the DMD 28 which corresponds to the IFOV of the selected segment of the DMD 26 is placed in the transmit mode. In this way, as the control unit 16 sequentially places segments of mirror elements of the DMD 26 in the transmit mode, the receiver assembly 14 operates as a moving iris, letting through desirable (e.g., non-scattered) photons from the target surface while blocking most or all of the scattered light from reaching the photocathode 50. Programmability of the DMD 28 also enables the system 10 to adapt to scan deviations. These features alleviate the need for sophisticated optical synchronization, as has been required in the case of systems operating with steerable mirrors, as well as the need to use a spinning aperture to account for cross-axis scan deviations.

The transmission path 22 extends from the collector lens 42 which receives photons emanating from the surface S illuminated by the laser source 19. The path 22 continues to the receiver DMD 28 such that the surface 56 of the DMD 28 which faces the lens 42 receives the light signal 21. All of the reflective surfaces of the mirror elements 30 of the DMD 28 may receive a portion of the light signal 21. As discussed above, with segments of mirror elements of the DMD 28 sequentially placed in the transmit mode by the control unit 16, portions of the light signal 21 are sequentially reflected from the surface 56 by different segments of mirror elements 30 so that the transmission path 22 extends from the reflective surface 56 of the DMD 28, through the magnifying lens 52 to a reflective surface 60 of the reshaping DMD 54. The reshaping DMD 54 and the magnifying lens 52 are used to reshape the IFOV to any desired geometric region. To effect this functionality the control unit 16 defines mirror segments comprising elements 30 of the DMD 54 which correspond to those spatial regions in the field of view having undesirably high levels of backscattering. According to embodiments of the invention the control unit configures the defined segments in a blocking mode while all other mirror elements 30 are placed in the transmit mode. With this configuration the spatial regions having undesirably high levels of backscattering are removed from the field of view before the light signal propagates to the photomultiplier tube 48. Accordingly, only portions of the light signal 21 containing acceptably low levels of backscattering are reflected by those mirror elements of the DMD 54 which the control unit selects to be in the transmit mode, thereby allowing those portions of the light signal to propagate along the transmission path 22 and through the focusing lens 46 so that the condensed light signal 21 strikes the photocathode 50 of the photomultiplier tube 48. The analog voltage output from the photomultiplier tube 48 is sent into the analog-to-digital converter 33 in the central control unit 16 for data collection and post processing. Another feature of the illustrated embodiment is that all of the light which can be transmitted from all of the mirror segments 30 on the reshaping DMD 54 can be focused on the photocathode 50 of the photomultiplier tube 48. Consequently only one photomultiplier tube 48 is required in the system 10. This feature facilitates further reduction in system size and cost.

Figure 5:
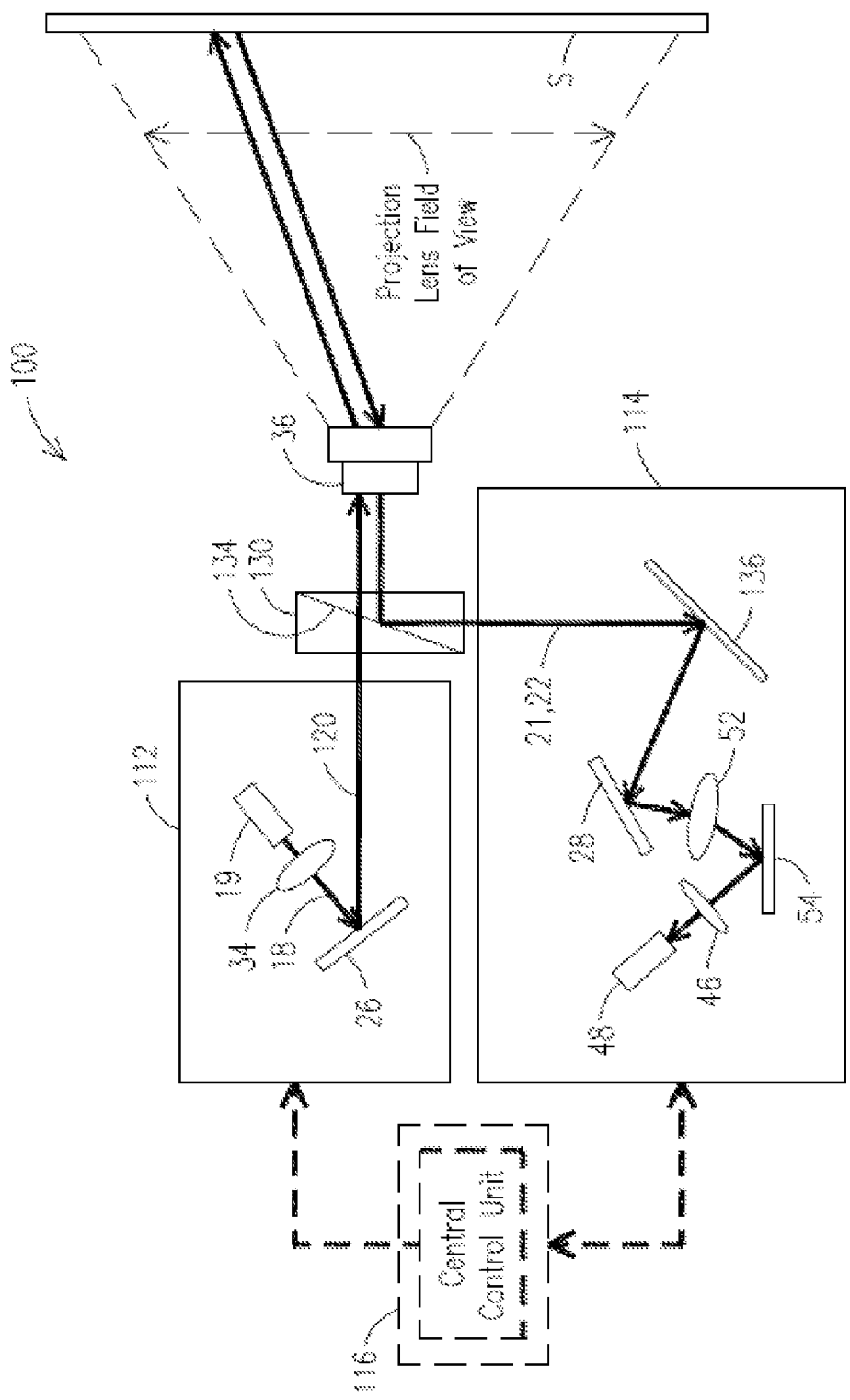
FIG. 5 illustrates an imaging system according to another embodiment of the invention.

FIG. 5 illustrates an imaging system 100 comprising a transmitter assembly 112 and a receiver assembly 114 operable under the control of the central control unit 16 as described with respect to FIGS. 1-4. In this regard, like reference numbers used for the features of the system 10 denote like features in the system 100. The transmitter assembly 112 transmits a light beam 18 generated by a laser source 19 which propagates along an outgoing optical beam transmission path 120 as indicated by arrows to a target surface, S. The receiver assembly 114, receives a light signal 21 reflected from the target surface S which propagates along a return (receiving) optical signal transmission path 122 as indicated by arrows. The transmitter assembly 112 includes the transmitter DMD 26 positioned in the outgoing beam transmission path 120 and the receiver assembly 114 includes the receiver DMD 28 positioned in the return signal transmission path 122. The system 100 does not include a collector lens 42 as a distinct component of the receiver assembly 114. Rather, the projection lens 36 is an element common to both of the transmission paths 120 and 122. Functionally the optical transmission paths 120 and 122 are each the same as a corresponding one of the paths 20 and 22. However, in the path 122 the light signal 21 propagates from the surface S through the projection lens 36 instead of passing through a collector lens 42. This arrangement is effected with positioning of a Total Internal Reflection (TIR) prism 130 placed in a segment of the transmission paths between the lens 36 and the two assemblies 112 and 114 so that the laser light beam 18 passes from the transmitter DMD 26 through the prism 130 to the projection lens while an internal surface 134 of the prism 130 reflects the light signal 21, emanating from the surface S and passing through the projection lens 36. The light signal 21 is reflected by the internal surface 134 to propagate to a mirror 136 which reflects the light signal 21 to the receiver DMD 28.

Thus the two optical paths share a common segment extending from the prism 130 to the lens 36 and to the target surface S. By adding the TIR prism 130 in the optical paths, the light beam 18 emitted from the transmitter assembly 112 illuminates the target surface S and the light signal 21 reflected back from the target surface S is directed into the receiver assembly 114.

Microdisplay devices other than DMD's, such as LCOS or HTPS devices, can be used in the systems 10 and 100 or variations thereof. The same optical configurations as shown in the figures can be used without change for several reflective type devices such as LCOS and MEMS scanning mirror devices. When incorporating a transmission type HTPS device, the laser source 19 and the photomultiplier tube 48 may be placed behind the HTPS panels. In the illustration of the systems 10 and 100 only one level of magnification is provided by cascading the one reshaping DMD 54 in the receiver assembly 14 or 114. However, multiple stages of magnification can be achieved by cascading two or more shaping DMD's 54 in the receiver optical path.

Compressive Sensing (CS) is a known framework for the simultaneous sampling and compression of sparse, and therefore compressible, signals using incomplete, non-adaptive linear measurements. This framework was previously described in D. Donoho, "Compressive Sensing," IEEE Trans. Inform. Theory, vol. 52, pp. 1289-1306, 2006; E. Candes and T. Tao, "Near optimal signal recovery from random projections: Universal encoding strategies?," IEEE Trans Infom. Theory, vol. 52, pp. 5406-5425, 2006; and E. Candes, "Compressive Sensing,", Proc. Int Cong. Mathematicians, vol. 3, pp 1433-1452, 2006, where the contents of each of these are herein incorporated by reference in their entirety. Based on this framework, an N-pixel signal $$X=\{X(n), n=1,2,\ldots N\}$$

is said to be K-sparse if there exists an N-dimensional sparsifying basis $$\Psi=\{\psi_1,\psi_2\ldots,\psi_N\}$$

and if $$X=\Psi a,$$

where the N×1 vector a contains K<<N non-zero entries.

CS theory states that if such a K-sparse basis exists for X, then X can be recovered with overwhelming probability using more than M=O(K log N) incoherent linear measurements:

$$Y=\Phi X=\Phi\Psi a,$$

where Y is a M×1 vector and $\Phi$ is a M×N matrix that is incoherent with the sparsifying matrix $\Psi$. See, again, E. Candes, "Compressive Sensing,", Proc. Int Cong. Mathematicians, vol. 3, pp 1433-1452, 2006. The matrix $\Phi$ is referred to as the measurement matrix, as described in E. Candes and J. Romberg, "Robust Signal Recovery from Incomplete Observations," Proc. ICIP, pp. 1281-1284, 2006, the contents of which are herein incorporated by reference in their entirety.

The incoherent property can be satisfied if the maximum magnitude of the elements of $\Phi\Psi$ is small, as noted in L. Gan, T. Do and T. Tran. "Fast compressive imaging using scrambled block Hadamard ensemble", Proc. EUSIPCO, 2008, the contents of which are herein incorporated by reference in their entirety. This condition can be achieved if $\Phi$ is random based, such as in a pseudo-random sequence, Bernoulli binary vectors or scrambled block Hadamard Ensemble (as described in M. Duarte, M. Davenport, D. Takhar, J. Laska, T. Sun, K. Kelly and R. Baraniuk, "Single-Pixel Imaging via Compressive Sensing," IEEE Signal Processing Magazine, vol. 25, pp. 83-91, 2008, the contents of which are herein incorporated by reference in their entirety), whereas K-sparse sparsifying basis $\Psi$ exists for many signal types, for example, natural images are sparse in Fourier, DCT or wavelet domain, a property exploited in the compression standards such as JPEG and JPEG2000. The $l_1$ norm minimization (as described in E. Candes and J. Romberg, "Sparsity and incoherence in compressive sampling," Inverse Problems, vol. 23, pp. 969-985, 2007, the contents of which are herein incorporated by reference in their entirety) can recover a (therefore X) from the measurements Y:

$$\hat{\alpha} = \mathrm{argmin}|a|_1 \qquad (1)$$
$$\text{subject to } Y = \Phi\Psi a$$
$$\text{where}$$
$$\|a\|_1 = \sum_{i=1}^{N} |a_i|$$

is the $l_1$ norm of a. Such an optimization problem is called basis pursuit.

The application of CS theory in image and video applications, or Compressive Imaging (CI) is one area of extensive interest. In addition to the aforementioned sparsifying basis, the image gradient sparsity can also be exploited via minimization of the image total variation (TV). For a digital image X, at pixel location $x_{ij}$, the discrete Gradient $D_{ij}(X)$ is defined as:

$$D_{ij}(X) = \begin{pmatrix} D_{h;ij}(X) \\ D_{v;ij}(X) \end{pmatrix} \qquad (2)$$
$$D_{h;ij}(X) = x_{i+1,j} - x_{i,j}$$
$$D_{v;ij}(X) = x_{i,j+1} - x_{i,j}$$

Then the TV of X is the sum of the magnitudes of $D_{ij}(X)$ at every point in X:

$$TV(X) = \sum_{ij} \sqrt{D_{h;ij}(X)^2 + D_{v;ij}(X)^2} \qquad (3)$$

TV minimization with quadratic constraints has been shown to provide better visual quality than that h optimization [12] when recovering images from noisy observations:

$$\min TV(X) \qquad (4)$$
$$\text{subject to } \|\Phi X - Y\|_2 \le \varepsilon$$

So far CS based imagers have been developed for various research disciplines. Among them, one pixel cameras and variations thereof are the earliest implementation, such as that described in Duarte et al.

Figure 6A:
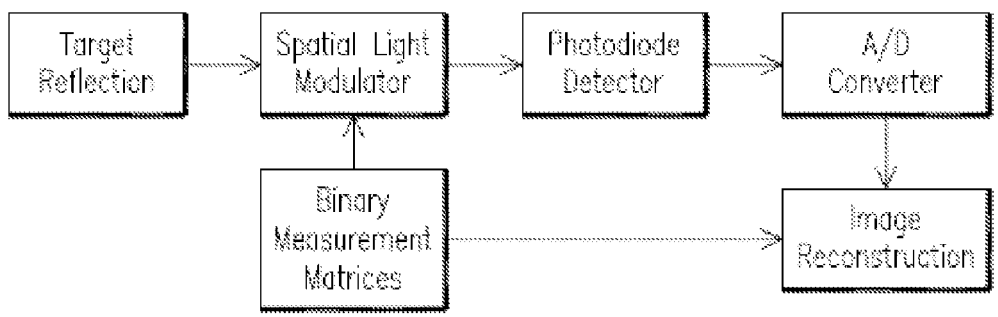
FIG. 6A is a flow diagram which illustrates an architecture for a one pixel compressive sampling camera.

The target reflection is modulated with a series of measurement basis $\Phi$; and the measurement for each of the bases is recorded by a photon counter. M measurements $$Y=\{y(l), l=1\ldots M\}$$

are obtained in serial. $\Phi$ and Y are then used as inputs to an optimization reconstruction process to recover á and the image X. An active illumination based one pixel camera was also reported in Duarte et al. The flow diagram of FIG. 6A illustrates an exemplary one pixel CS camera architecture.

Figure 6B:
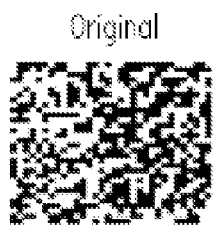
FIGS. 6B and 6C illustrate a binary measurement pattern before and after propagation through water.
Figure 6C:
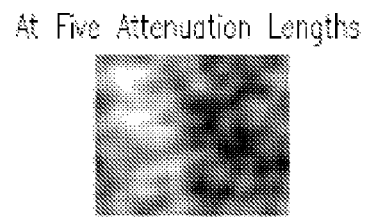

According to the invention, a CS based underwater imaging system is presented for use in an underwater environment, where any imaging system is subject to the dispersive water medium. There is not an exception for a CS based imaging system. The binary measurement matrices generally used in an over-the-air imaging system will lose most of the detail after propagating short distances in the water. FIGS. 6B and 6C illustrate degradation of an image shown in FIG. 6C at five attenuation lengths as shown in FIG. 6C, which renders the spatial light modulation ineffective.

Figure 7A:
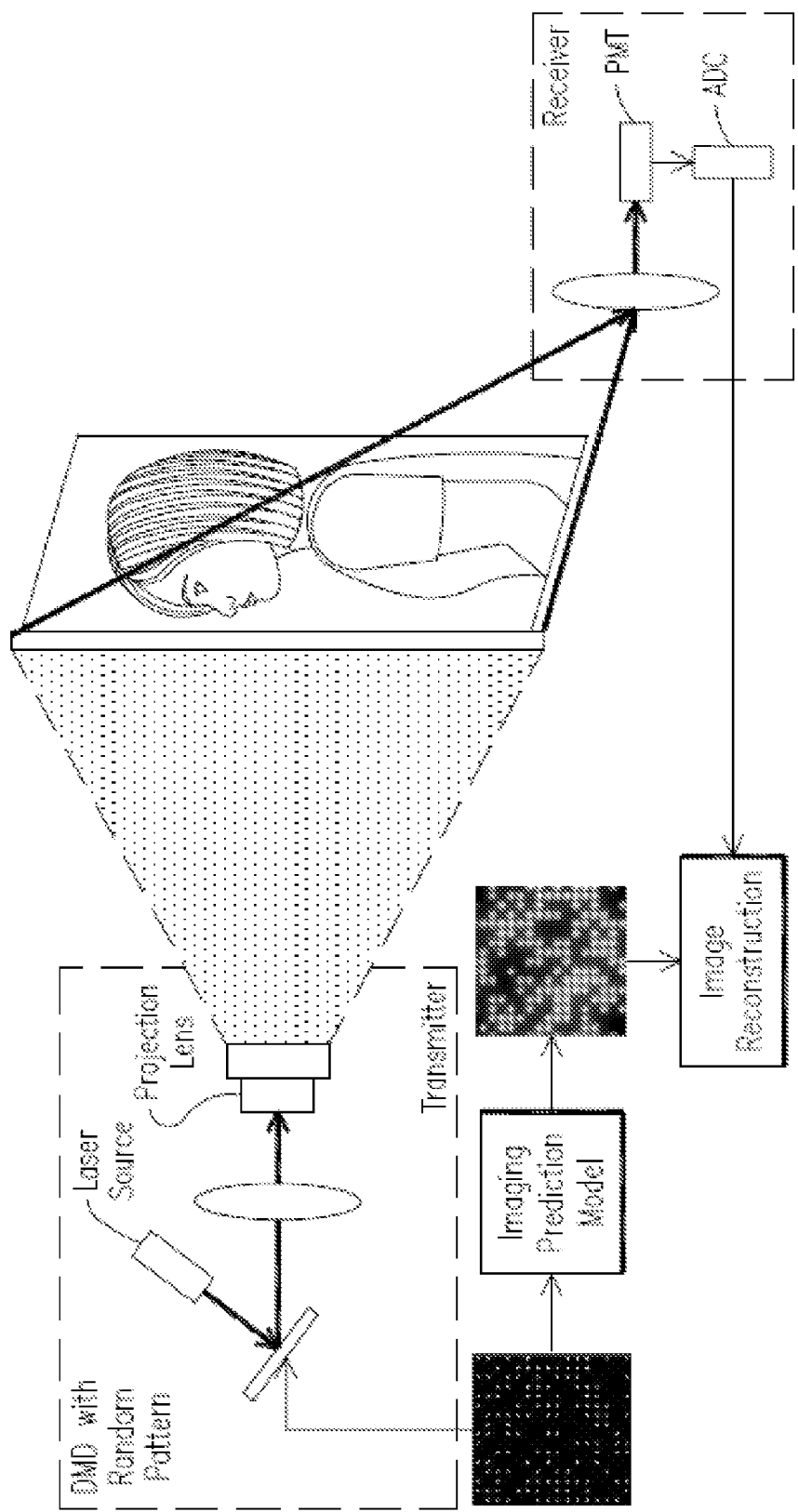
FIG. 7A illustrates a design of a CS based underwater laser imager concept according to the invention and FIG. 7B is a flow chart for the same.
Figure 7B:
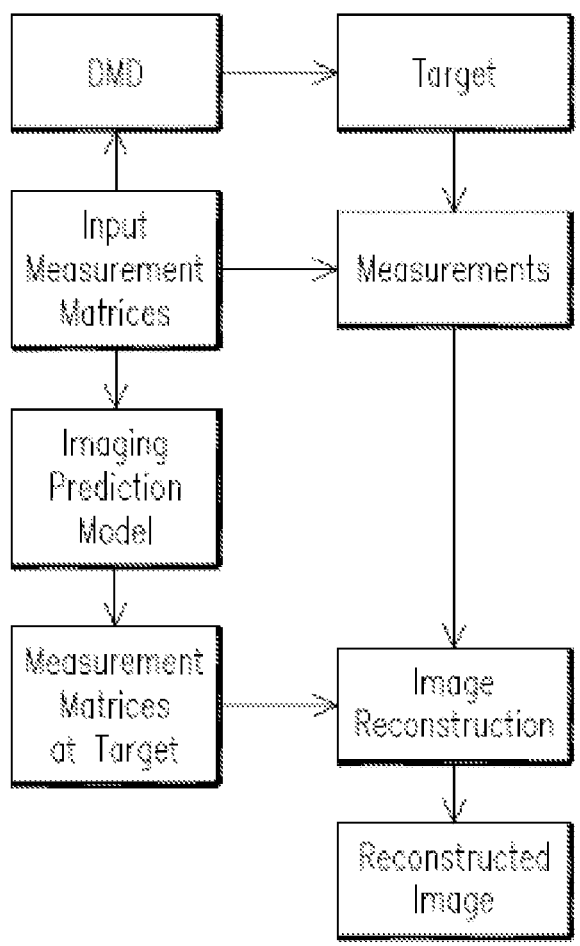
Figures 8A, 8B, 8C:
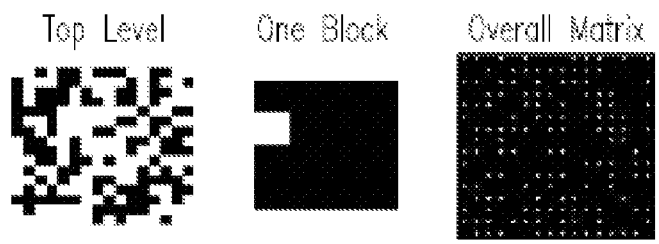
FIGS. 8A-8D illustrate Multi-scale measurement matrix designs.
Figure 8D:

FIG. 7A illustrates a design of a Compressive Sampling (CS) based underwater laser imager according to the invention and FIG. 7B is a flow chart for the same. Referring to the flow chart of FIG. 7B, input measurement matrices are loaded sequentially onto a spatial light modulator such as a DMD to modulate a CW or pulsed laser source to illuminate the target. The reflection is then measured using a photon detector such as photomultiplier tube or photodiode and converted to digital data stream using an analog to digital converter. The original measurement matrices are run through an imaging prediction model to predict the measurement matrices at the target. The predicted measurement matrices and the measurement are then used to re-construct the target image. Designs according to FIG. 7 enable operation of the CS based imager in an underwater environment by incorporating the following four concepts:

A1) Multi-Scale Measurement Matrix Design

With reference to FIGS. 8A-8D, the dither pattern is divided into small blocks of pre-defined size. Only one "on" pixel will be present within each block and the location of this pixel within the block $\{b_{ij}\}$ will be generated from a pseudo-random sequence $\{p_{1i}\}$. The polarity of each block will be determined by a second pseudo random sequence $\{p_2\}$. The overall dither pattern will be the product of $\{p_2\}$ and $\{p_{1i}\}$:

$$\begin{cases} x(i, j, k) = 1, & \text{iff } p_{1i,j}(k) * p_2(i, j) = 1 \\ x(i, j, k) = 0, & \text{otherwise} \end{cases} \quad (5)$$

where x is the pixel intensity, i,j are the block indices, and k is the pixel location within a block.

A2) Model Assisted Image Reconstruction

Figures 9A, 9B:
FIGS. 9A and 9B provide a comparison of reconstructed image using binary measurement matrices and model predicted matrices at 7 attenuation lengths.

Measurement matrices that actually modulate the target surface S are not the original binary measurement matrices. Instead such patterns result after propagating in the water from the source to the target surface. The measurement matrices used in image reconstruction should be the actual pattern which modulated the target. A radiative transfer model such as EODES [11] can predict the resultant measurement matrices to be used in image reconstruction. FIGS. 9A and 9B illustrate a comparison of a reconstructed image using binary measurement matrices and model predicted matrices at seven attenuation lengths.

A3) Polarity Flipping to Reduce Volume Backscatter

With Polarity Flipping each pattern can be loaded twice, first with mirror "on" transmit mode (corresponding to a digital "1"), and then with mirror "off" blocking mode (corresponding to a digital "0"). The difference between the two PMT readings will be the coefficient for a bipolar (1,−1) base vs. a (0,1) base since the angle of the illumination will be fixed during all of the measurements. In addition, all random measurement bases will consist of about half of "on" position and, therefore, the contribution of the backscattering to the coefficient can be regarded as Gaussian noise with a constant non-zero mean. Therefore, the above polarity flipping can essentially cancel out the impact of the backscattering. This can reduce the impact of the backscattering since a similar number of mirrors will be on during the polarity flipping. Thus the volume backscattering will be the same in the two runs and their difference helps to cancel out or reduce the backscattering levels.

A4) Multiplexing to Speed Up Measurements

One disadvantage that might be associated with CS based imaging systems is that measurements would need to be acquired sequentially. This slows down the system response time. The number of sufficient measurements M is proportional to the logarithm of total pixels of the image N: $M \propto \log_2(N)$.

Figure 10:
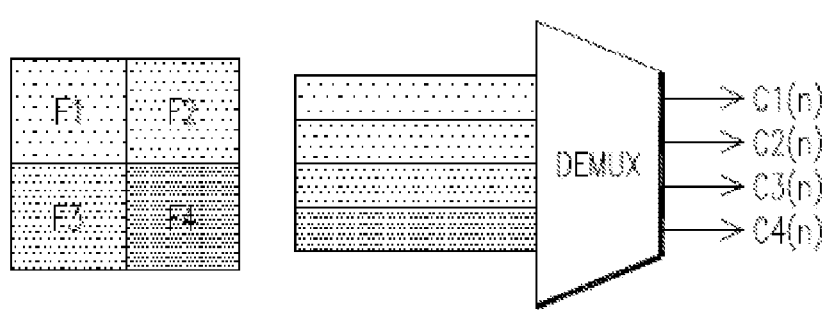
FIG. 10 illustrates spatially multiplexed measurement.

With reference to FIG. 10, another feature of embodiments of the invention is the illumination of different regions with the laser intensity modulated with different frequencies and demodulating the laser signal at the receiver to recover the coefficients corresponding to each sub region. This spatially multiplexed measurement allows for a reduction in the required measurements M, and therefore speeds up the image acquisition time. It provides a novel way to speed up CS measurements which otherwise create a bottleneck in most CS based imaging systems.

Besides providing the ability to compress data during image acquisition, CS has several additional benefits for underwater serial laser imaging systems. A Flexible Imager Configuration is provided having a simple illuminator design and most of the computation load is at the receiver end, which is desirable in a multi-static geometry. The CS-based system works when there is no line-of-sight between the target surface and the photomultiplier tube. The imager configuration is applicable in near mono-static geometries. The resulting systems are reliable, compact and of low cost, using commercially available solid state spatial light modulators and providing compression during acquire which permits lower speed electronics and reduced levels of storage. Such systems have relatively good Photon Efficiency/Concentration, using a "bucket" photon collector—photomultiplier tube, but the efficiency is less than that of a LLS due to photon loss during DMD modulation. Pixel photon concentration depends on compression ratio. Another advantage of the technique is that desirable image resolution can be achieved at higher speed platforms without solely relying on increasing the laser repetition rate.

Backscattering is mitigated by polarity flipping, applicable to both CW and pulsed laser. This is unique to CS imagers. Conventional pulsed lasers and range-gated receivers also work for CS imagers. The methodology provides an intrinsically encrypted process because access to the same measurement matrices is necessary in order to recover the image. This is desirable for integrated distributed imaging and communications applications.

It is also possible to provide long range high resolution imaging by integrating the imaging system with long range low bandwidth underwater communication devices, such as acoustic communication devices, without requiring additional compression/decompression hardware.

The foregoing described concepts are also applicable in the context of a passive implementation, where the target to be imaged is illuminated by a pulsed or CW laser. At the receiver a series of binary measurement basis patterns are loaded onto the Spatial Light Modulation device. The photomultiplier tube reading will be the coefficient of each individual basis. These amplitudes can be used in an optimization-based reconstruction, followed by an inverse transformation to recover the spatial image intensity of the target surface S.

Another application of using digital microdisplay devices such as a DMD, also related to imaging through a turbid medium, is the measurement of the scattering characteristics of a medium. These measurements could include the shape and magnitude of the Volume Scattering Function (VSF), the particle size distribution derived thereby, or other angularly resolved scattering parameters. Accuracy and usefulness of this type of measurement is most often limited by the spatial resolution of the receiver configuration and the sensitivity and dynamic range of the light sensing device.

Figure 11:
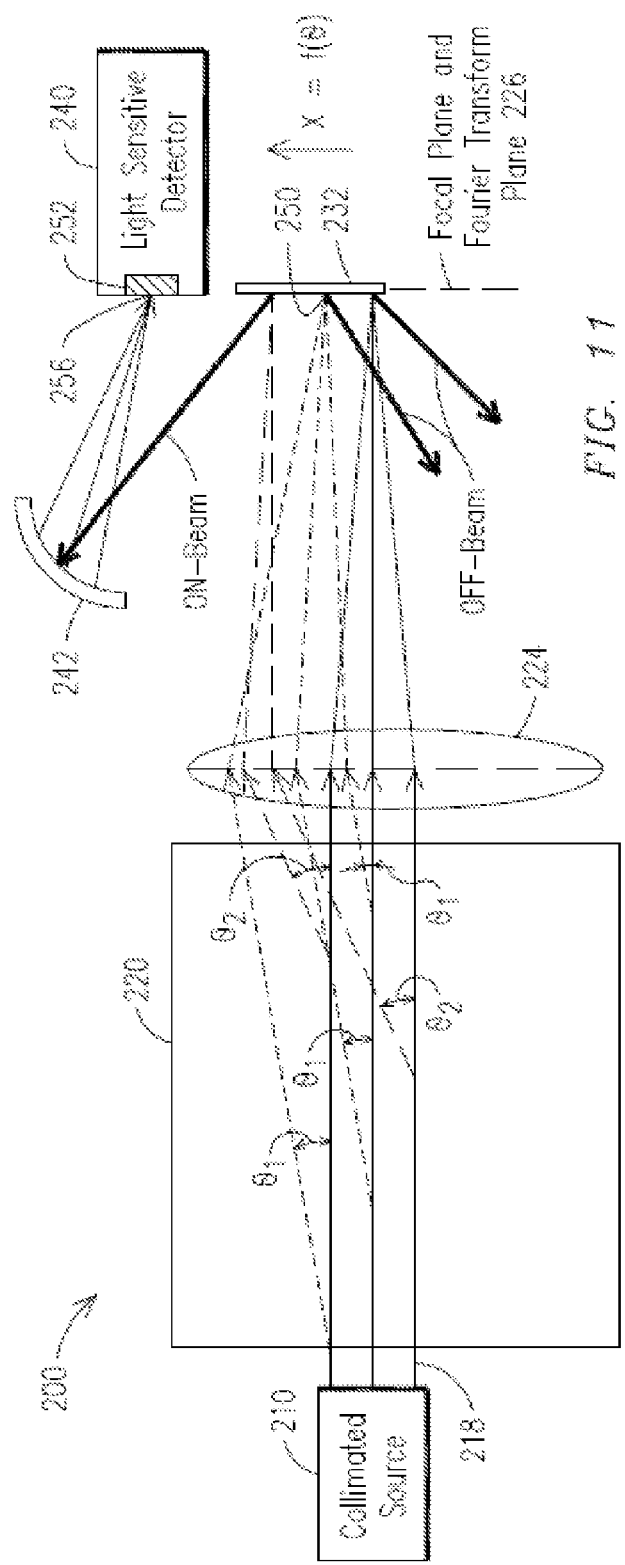
FIG. 11 is a schematic diagram illustrating a scattering sensor system according to an embodiment of the invention.
Figure 12:
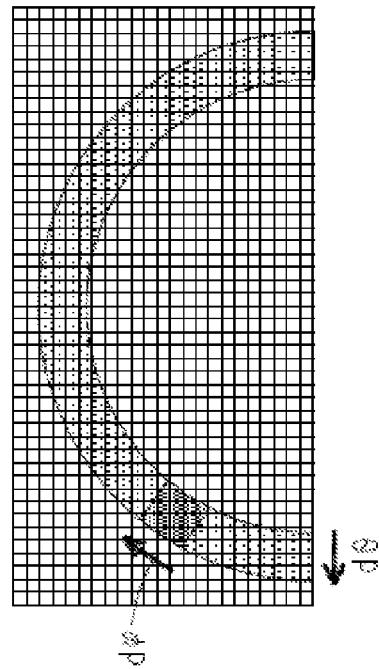
FIG. 12 illustrates an ON-region in an array of mirror elements of a DMD in relation to a scattering angle range.

A method for measurement of the scattering characteristics of a medium employs an optical system such as the exemplary sensor system 200 depicted in FIG. 11. The source 210 transmits collimated incident light 218 which experiences spatial and temporal dispersion while traveling through a scattering medium 220. The spatial distribution of the received light on the light sensitive detector is a function of the VSF of the particle ensemble, absorption characteristics of the suspension, and concentration of the particles. Transmitted and scattered light are both focused through the lens 224. The focal plane 226 (indicated by a hatched line) is also the Fourier transform plane, on which the angular information incident on the lens 224 is transformed to spatial frequency. A DMD 232 is positioned along the focal plane 226 to control the direction of the reflected light field. Some of the light 218 (referred to as ON-beam) is directed to a very sensitive detector 240, such as a photomultiplier tube, via collecting optics 242 (e.g. a hemi-ellipsoidal reflector depicted in FIG. 11). All other light (referred to as OFF-beam) is reflected elsewhere or discarded (e.g. by placing elements in a blocking mode), or collected by a separate light sensitive device e.g., for direct transmission measurements. The light initially scattered by interaction between the incident photons and the particles at a specified angle can be measured by selecting only certain elements within the DMD array to be turned on at a time. On the Fourier plane, this sub-array corresponds to the region where all the light scattered at angle $(\theta,\phi)$ falls. FIG. 12 illustrates an ON-region 260 in an array of mirror elements of a DMD 232 in relation to a scattering angle range to provide an example of how the array of mirror elements can be divided into specific two dimensional sub-arrays, or regions, corresponding to specific scattering angle ranges. Mirror elements in the ON-region are shaded to indicate they are in the transmit mode while unshaded regions correspond to mirror elements in the blocking mode, constituting an OFF-region. The width, referred to as d$\theta$, with reference to a polar coordinate system, of the ON-region can be adjusted for individual applications. Some particle size measurements would require d$\theta$ to increase logarithmically.

Along the ON-sub-array, light incident on each element is reflected in different directions depending on the azimuth angle $\phi$. To circumvent this dependency, the reflected light is collected by a dual-focal point ellipsoidal reflector, or similar means. The DMD 232 is located on the first focal point 250, while the photocathode 252 of the photomultiplier tube 240 is located on the second focal point 256, where all the light from all azimuth angles $\phi$ is condensed. Therefore, the PMT is responding to the integrated power from all azimuth angles $\phi$. However, if scattering in more refined resolution in the solid angle range is required, the azimuth range can be selected by selecting only a small section of the annular de sub-array. Similarly, embodiments of the invention could consist of a near collocated transmitter and receiver optics, which would provide fine angular scattering in the backward direction.

Significant improvements to the state-of-the-art are the ability of the sensor system 200 to adjust the dynamic range in real-time and in a linear manner, and also, in general, the ability to increase the dynamic range. This could be achieved by modulation (in case of continuous wave applications) or turning off (in pulsed applications) some of the mirror elements in the scattering angle regions, where the scattered intensity is very high compared to other regions, and factoring the decreased irradiance at the light sensitive device, e.g., the photomultiplier tube 240, in the post-processing stage.

In pulsed source applications, the method of using an ultra-fast single-element detector in conjunction with a DMD enables accessing near-simultaneous temporal and spatial information on the scattered light field. This information is especially valuable in highly scattering environments, where multiple scattering is the source for significant, and often limiting, noise impairing the performance of imaging and communication links.

The primary benefit of the innovation is the ability to use a fast, sensitive single-element light sensitive device with a high spatial resolution and minimal processing requirement in scattering measurement applications. The ability of real-time optimization of the spatial resolution makes the system ideal for remote sensing and unmanned operations. The ability of the described system to respond to variations in the dynamic range requirements is highly beneficial, relating to the measurement and observation of medium optical properties in environments, where accessibility or ambient light levels are low or very variable. The near-simultaneous temporal and spatial (angular) measurement gives access to useful information on properties of turbid media, which could be used to optimize performance of remote imaging and communication systems. Summarily features in accord with the invention include: eliminating moving parts needed in prior system designs; reduced cost to maintain high precision optics; reduced system complexity; reduced measurements relative to those required in prior compressive sampling—based image system designs; and higher dynamic range as required for a volume scattering function (VSF) meter.

Embodiments of the invention have been described which simplify the system optics and electronics. For example the imaging systems 10 and 100 do not require moving parts or high precision optical alignment. The computation intensive reconstruction phase can be off-loaded to a central vessel or done off-line. It retains the "bucket collector" PMT type detector that is essential for lumen deficient imaging environments such as turbid waters. A CS based imager and methodology suitable for a low light environment has been described to reduce noise and interference from volume and forward scattering. The invention can also overcome motion artifact problems associated with serial imaging architectures. Further, an active CS illumination system does not require direct line-of-sight observation for the receivers, and can be advantageously used in a hi-static imaging environment. In one series of embodiments frequency multiplexing of the modulated laser reduces the time required for CS measurement.

In addition to the frame based CS active laser imaging system described above, an alternative line sensing design, incorporating key ingredients from the frame based approach above, has also been developed. In this line sensing architecture, the required measurements are taken on a line basis, rather than on a frame basis. Thus, the measurements are compatible with the near mono-static, moving platform imaging system configuration. One additional important concept to be incorporated into this design is the so-called Distributed Compressive Sensing (DCS) (D. Baron et al., "Distributed compressed sensing", Rice University, Depart. Electrical and Computer Engineering Technical Report TREE-0612, November 2006.) to exploit the high degree of correlation between successive lines. In a DCS implementation, each individual source within the group of correlated sources will be measured (i.e. encoded) independently using a series of random measurement matrices. However the group of sources will be jointly reconstructed by exploiting the joint sparsity of these sources to improve the reconstructed signal quality with same measurements for each individual source. In the various embodiments using DCS and line sensing, each line is be regarded as a signal source, and the statistical correlations or redundancy between adjacent lines are exploited, via a joint sparsity model, to further reduce the required measurement volume and improve the overall compression performance.

While the exemplary embodiment for this design will be directed to underwater laser serial imaging system (imaging Lidar), the concept can be extended to aerial imaging Lidar, medical imaging Lidar, and any other active serial imaging applications, such as laser printers.

Figure 13:
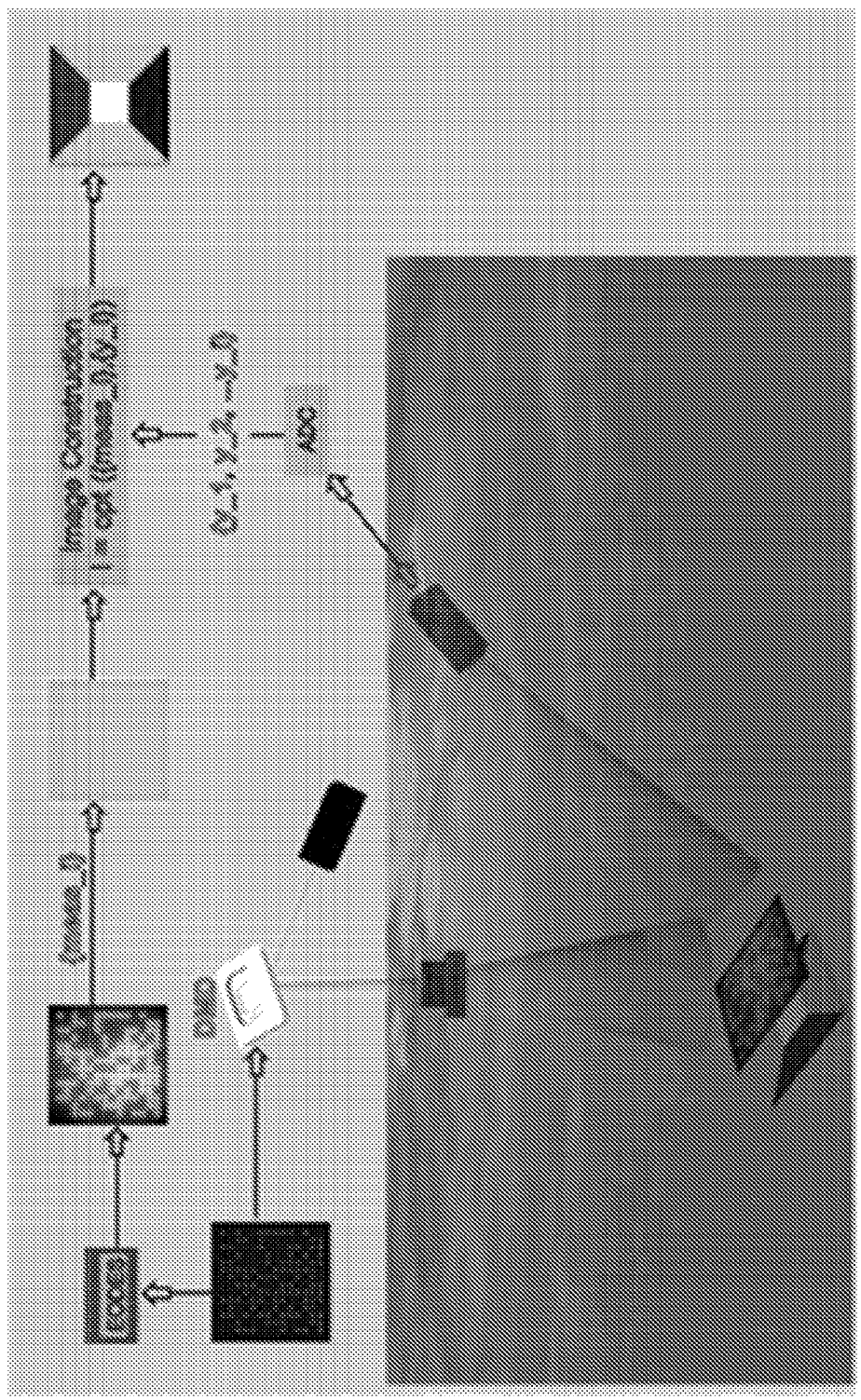
FIG. 13 shows a schematic of a Compressive Line Sensing Active Serial Imaging System according to the invention

The application of CS theory in underwater imaging systems provides a more compact, reliable and cost effective underwater serial laser imaging system using solid state SLM/microdisplay devices like DMD. Compared to conventional methods using a one-pixel camera, one major difference of this system architecture is that DMD is incorporated into the illumination path to modulate the incoming laser instead of the detector, as shown in FIG. 13, which illustrates a general schematic of a CS-based underwater laser imaging system. Furthermore, the constraints imposed on a CS imaging system due to underwater scattering medium were studied. Consequently, a new measurement matrix design, a volume backscattering reduction technique and the "model-assisted" image reconstruction concept were described to mitigate such constraints.

It should be noted that while the various embodiments with be discussed primarily with reference to a DMD, other SLM devices can be used in the various embodiments. In fact, one advantage of the various embodiments is that since 1D SLM devices are suitable for this technique, this substantially widens the list of applicable SLM devices. The devices can therefore include Grating Light Valve (GLV) device—a 1-D SLM device that is capable of up to 500K refresh rates or a scanning MEMS device. However, the various embodiments are not limited in this regard and other devices can also be used.

The various embodiments using line sensing provide a sensing system that is more compatible with the traditional survey platforms, where the images are acquired one line at a time and rely on platform motion as the second axis to complete the whole image. The work in by B. Ouyang et al. in "Underwater Laser Serial Imaging Using Compressive Sensing and Digital Mirror Device", SPIE, Vol. 8037, 2011 (hereinafter "Ouyang et al."), the contents of which are herein incorporated by reference in their entirety provide insight into the understanding of how to implement a CS based active imaging system suitable for an underwater environment.

Compressive Line Sensing Active Serial Imaging System

The exemplary system described below incorporates the basic concepts behind DCS technique to exploit the statistical dependency in the image formation process with the underwater CS imaging technique outlined in Ouyang et al. to combat challenges from the underwater scattering medium. FIG. 13 shows a schematic of a Compressive Line Sensing Active Serial Imaging System. The system of FIG. 13 is substantially similar to that illustrated in FIG. 7A, with the exception that illumination of a target area and image reconstruction is based on compressed line sensing.

B1) Relevant DCS Concepts (D. Baron et al. in "Distributed Compressed Sensing", Rice University, Depart. Electrical and Computer Engineering Technical Report TREE-0612, November 2006).

DCS is closely related to the distributed source coding theorem. This states that the minimum rate of independently encoding the statistically dependent sources is the same as the minimum rate of jointly encoding, with an arbitrarily small probability of error when jointly decoding is performed and the innovation of the sources, i.e., their differences are Gaussian, for both lossless and lossy with side information cases.

While the CS theory mostly addresses the intra-signal sparsity, DCS attempts to exploit the inter-signal redundancy in addition to the intra-signal sparsity among distributed and correlated sources through the establishment of the proper joint sparsity models (JSMs). Three different joint sparsity models have been proposed:

JSM-1—all signals $X_l$ consist of a sum of a common (sparse) component Z and an innovations component that is unique to each signal $Z_l$: $X_l = Z_c + Z_l$, l=0, 1 ... g.

JSM-2—all signals are constructed from the same sparsify basis, but the coefficient values can be different: $X_l = \Phi \theta_l$, l=0, 1 ... g.

JSM-3—an extension of JSM-1—all signals share the same non-sparse common components plus the innovation.

where g is the number of sources to be jointly solved.

JSM-1 has been extended further to the so-called generalized distributed compressive sensing (GDCS) where there may be disjoint common components among a subset of the sources within the group:

$$X_l = \begin{cases} Z_{c1} + Z_l, & \text{iff } l \in c1 \\ Z_{c2} + Z_l, & \text{iff } l \in c2 \end{cases}, l = 0, 1 \ldots g$$

B2) Extending DCS to Line Sensing Imaging System

Figure 14A:
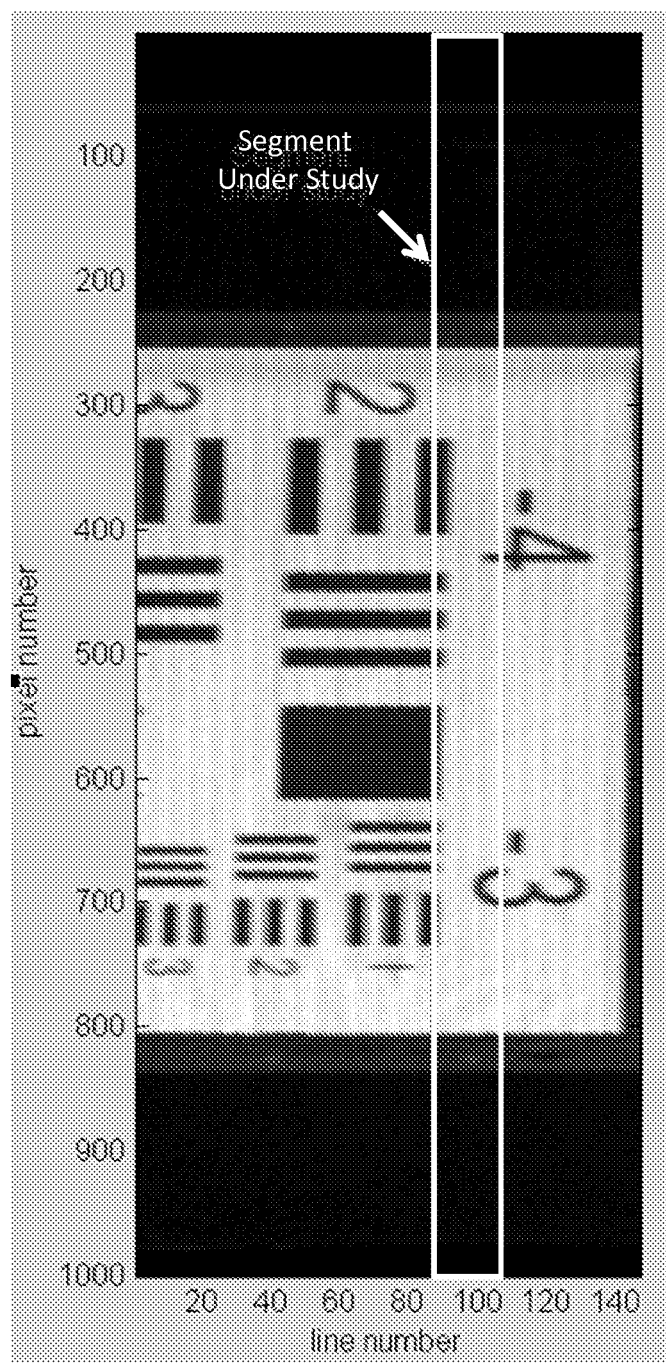
FIGS. 14A-14C are images and plots illustrating that the statistical dependency or correlation among adjacent lines according to the invention.
Figure 14B:
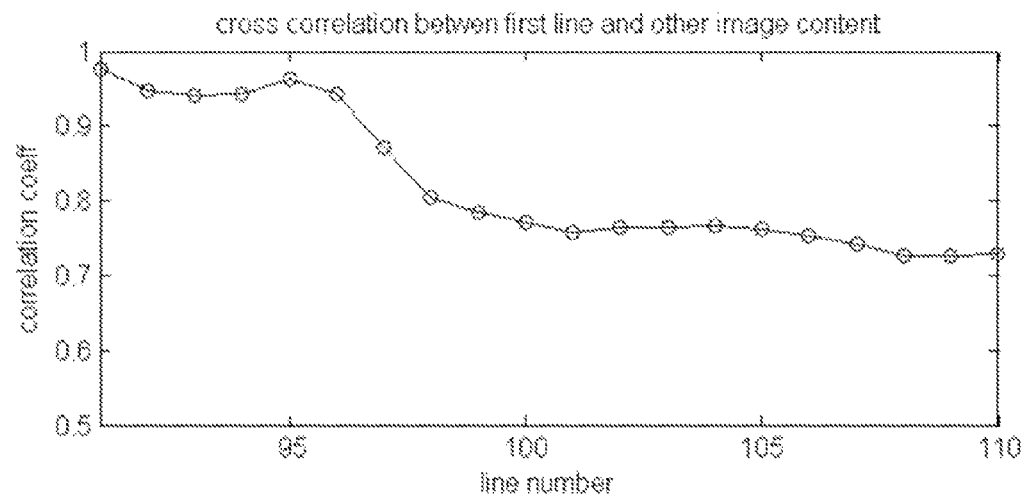
Figure 14C:
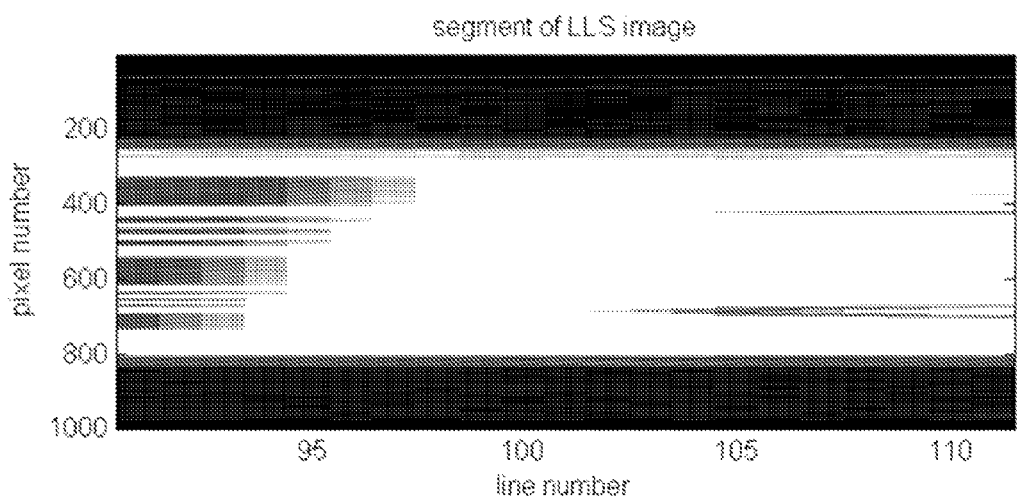

The group of correlated sources dealt with in the DCS theory shares some similarities with the LLS imaging Lidar. The statistical dependency or correlation among adjacent lines is strong, as shown in FIGS. 14A-14C. These figures offer a simplistic demonstration of such correlation using a segment of underwater laser line scan image of a technical target acquired in a Harbor Branch Oceanographic Institute (HBOI) test tank. FIG. 14A shows the resulting LLS image, FIG. 14B shows cross-correlation between a first line and other image content. As shown in FIGS. 14B and 14C, the cross correlation between first line and the subsequent 5 lines is very high. Furthermore, while the correlation did drop off after the first 5 lines, the pattern of intensity change indicates that there is still significant common signal component can further help to exploit the line-to-line statistical dependency. It is therefore conceivable such redundancy can be exploited by adopting the joint sparsity concepts described above into the line scan imaging Lidar context. Each line can be regarded as the equivalent of a source in the DCS context. A cluster of lines can be regarded as an equivalent of the group of sources. The measurements of each line will be acquired independently using pre-determine set of measurements matrices and reconstructing a group of lines jointly. The solver relies on the theoretical foundations established for DCS JSM-1 and GDCS. The validity of signal reconstruction with noisy and incomplete measurements has been previously studied. This is critical for underwater imaging applications to survey targets at extended scattering thicknesses where the noise level in the target reflection measurements can be very high.

The sensing process of one possible implementation can be described below:

$$Y = \Phi X = \Phi P \Psi \theta$$

Where $Y \in R^{M \times G}$ are the measurements of the group of lines;

$$\Phi = \begin{pmatrix} \Phi_1 & 0 & 0 \\ 0 & \ddots & 0 \\ 0 & 0 & \Phi_g \end{pmatrix}$$

is the measurement matrix for the g group of lines, and $$P = \begin{pmatrix} C_1 P_c & P_1 & 0 \\ C_2 P_c & \ddots & 0 \\ C_g P_c & 0 & p_g \end{pmatrix}$$

is a binary location matrix. Where $C_i$ are binary coefficients, if a DCS JSM-1 model is adopted, then $C_i = 1 \forall i$.

For GDCS model, then $C_i$ is determined by the following rule:

$$C_i = \begin{cases} 1, & \text{if } DC \text{ coefficients of line } i \text{ measurements} < th \\ 0, & \text{if } DC \text{ coefficients of line } i \text{ measurements} > th \end{cases}$$

$\Psi$ is the sparsifying basis, and $\theta$ is the value vector:

$$\theta = [\theta_c \theta_1 \theta_2 \ldots \theta_g]^T$$

Figure 15A:
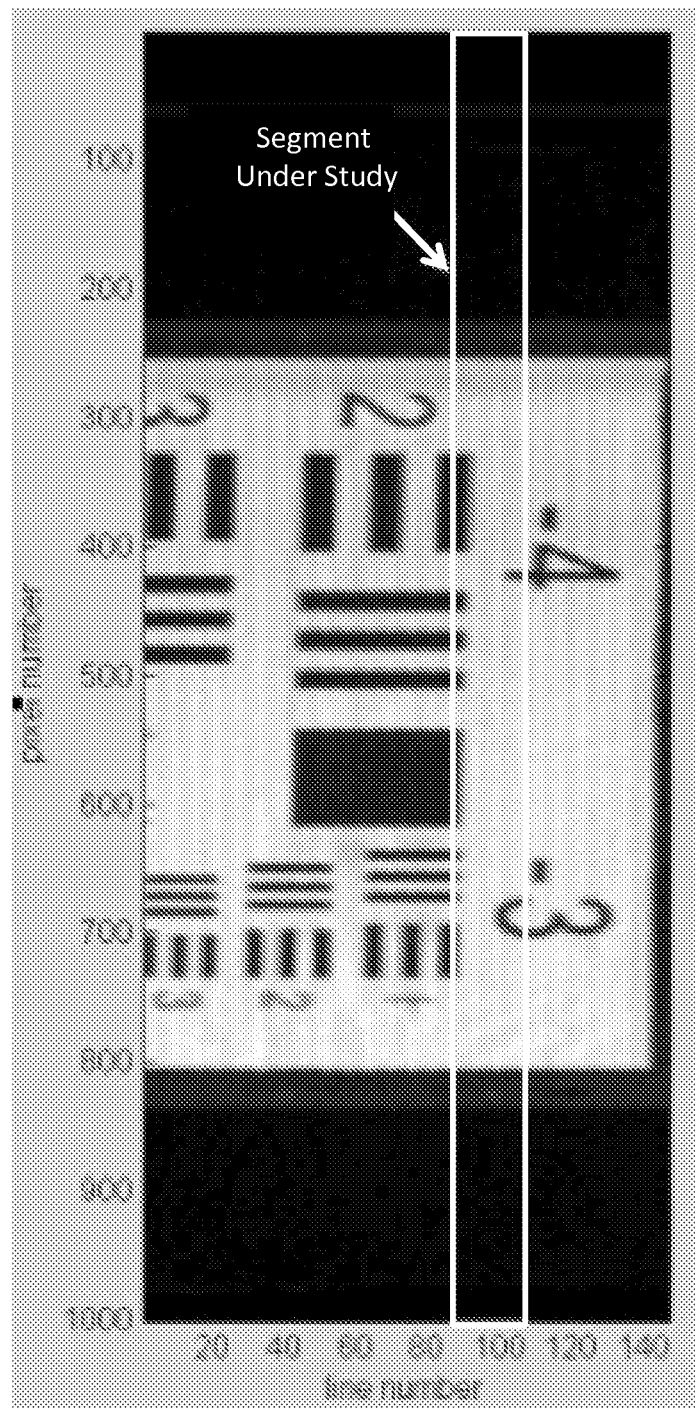
FIGS. 15A-15C are images and plots showing the setup and results of measurements of DC coefficients of the simulated measurements of the LLS segment of FIG. 14A according to the invention.
Figure 15B:
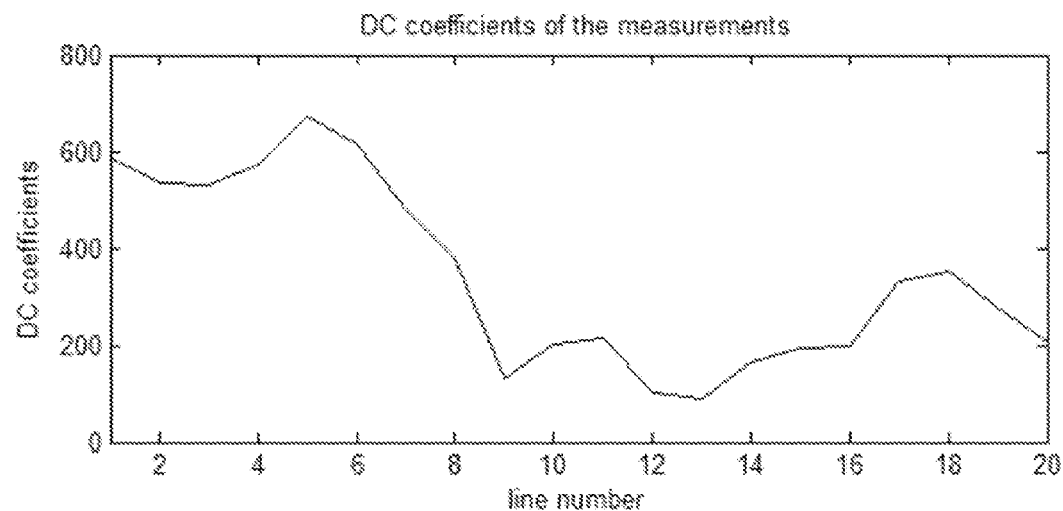
Figure 15C:
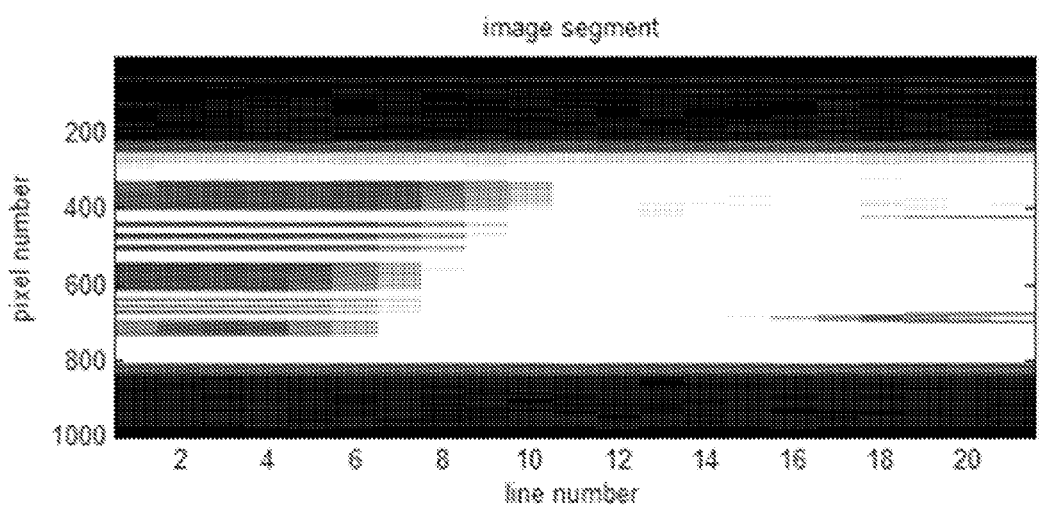

B3) Adaptive Determination of Group of Line Size Based on Measurements of DC Coefficient Another related issue is to determine the number of lines to be clustered in one Group of Line (GOL). One solution is to adopt a hard reset (i.e., group pre-determined number of lines). This is the approach adopted in most existing DCS applications. On the other hand, adapting GOL size based on the detection of significant changes from previous lines should help to ensure all lines within the group share significant common components and therefore improve the effectiveness of the solver. Such adaptation shares similarity with the adaptive I-frame in video compression applications. In this regard, an I frame adaptation criteria through monitoring the DC coefficient differences between frames since the DC coefficient contains the most entropy of the spatial block data can be used (H. Farouk, "MPEG Bit Rate Improvement Using Adaptive GOP", International Journal of Circuits, Systems and Signal Processing, vol. 1, pp. 8-11, 2007). A simple study was again conducted using the same segment of FIGS. 14A-14C in FIGS. 15A-15C by generating 100 measurements for each line (using pseudo-random patterns) and computing the corresponding DC value of these measurements for each line. As shown in FIGS. 15B and 15C, the variation of the DC coefficients correlates strongly with the content variation. Therefore the DC coefficients can be used as an indicator of the correlation of adjacent lines One virtue of DCS (and GDCS) paradigms is that each measurement is independent with each other. Therefore if significant change is detected by examining the DC coefficients of the measurement vector as described above, a new GOL can be prompted. Because SLM devices can sustain high refresh rates (i.e. DMD can sustain a measurement rate of 40000/sec) and each line segment will be sampled with an equal number of measurements, such GOL promotion can be done in real time. An alternative implementation may follow the GDCS method, where a fixed (sufficiently large) GOL is adopted whereas the actual common components among a subset of the lines within the GOL is determined via evaluation of the DC coefficient of the measurements.

Another related parameters is the number of measurements per line, in the current application setting, the number of measurements per line is essentially the compression ratio. As such, there is a tradeoff between the increase of compression ratio (i.e., smaller number of measurements/per line) and the increase of the GOL (i.e. the lines with low correlations are grouped and solved together) to achieve the optimum image quality balance. For example with 1:2 compression (i.e., acquire 256 measurements for an image with 512 horizontal pixels), each line can be reconstructed independently (i.e., GOL=1); with 8:1 compression (i.e, 64 measurements/line), GOL=5-7 may be required; with 32:1 compression (i.e. 16 measurements/line), GOL will required to be increased to 15-19. This optimization is illustrated with respect to FIG. 16 and FIGS. 17A-17F.

Figure 16:
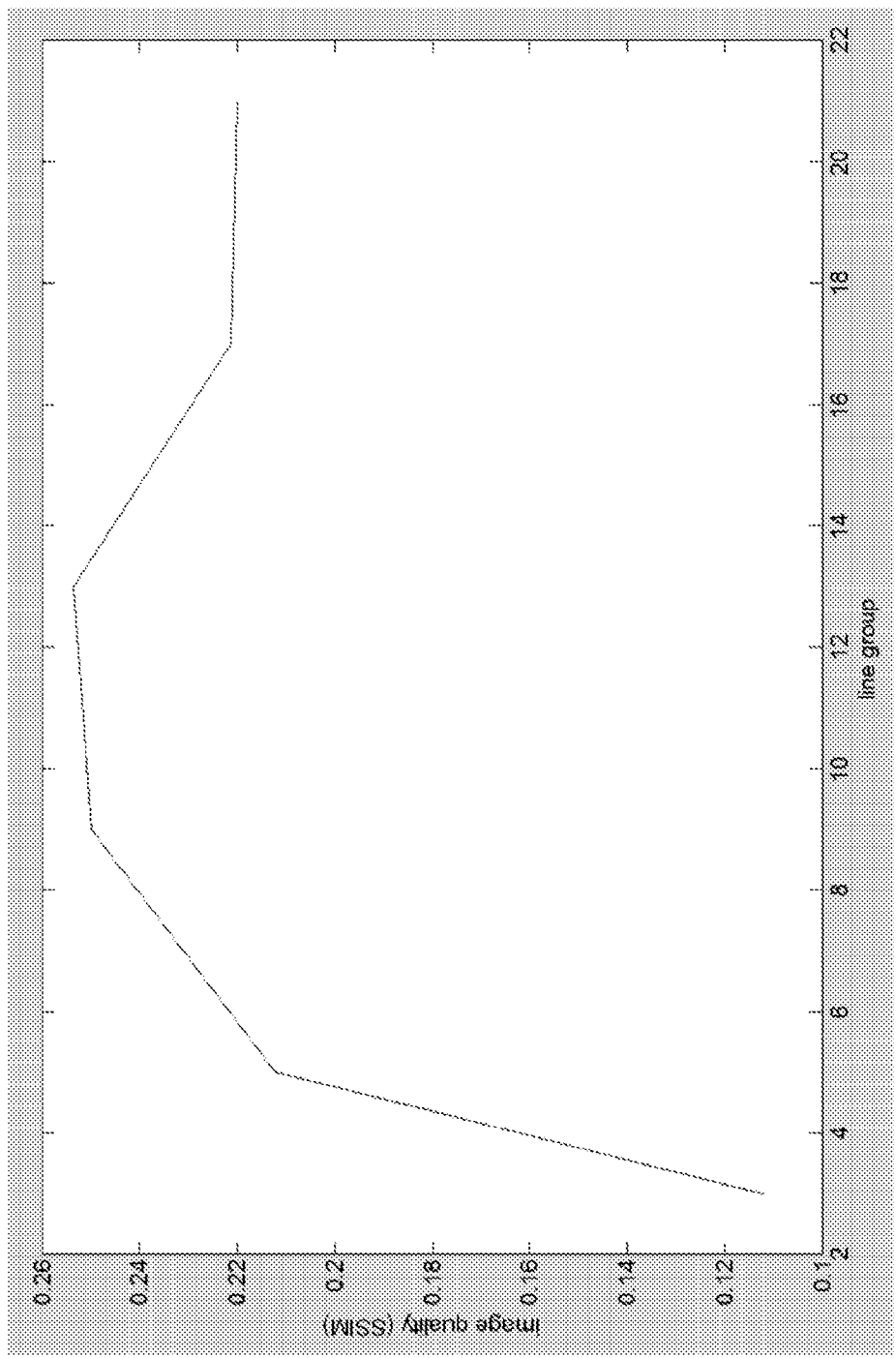
FIG. 16 is an x-y plot of image quality as a function of GOL for a 16:1 compression ratio for an image resolution of 512× 512 pixels in clear water according to the invention.
Figure 17A:
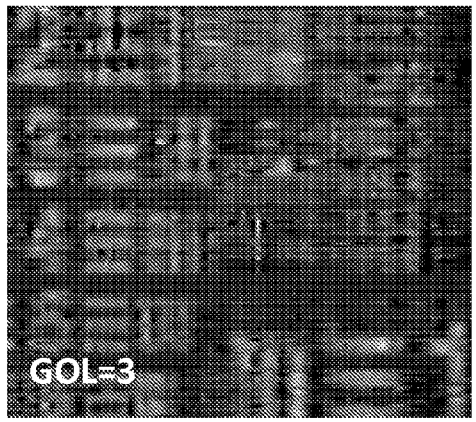
FIGS. 17A-17F show the resulting images for GOL=3, 5, 9, 13, 27, and 21, respectively, according to the invention.
Figure 17B:
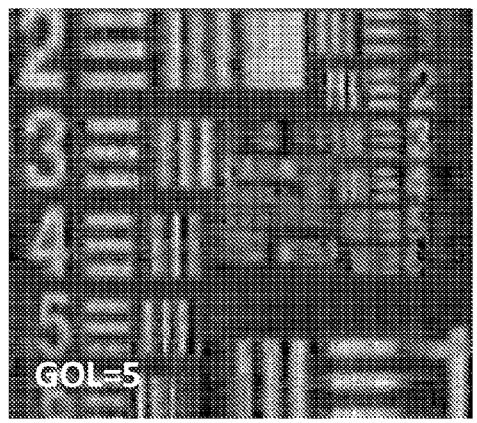
Figure 17C:
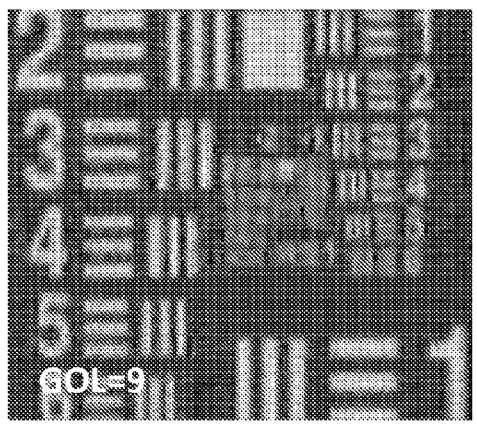
Figure 17D:
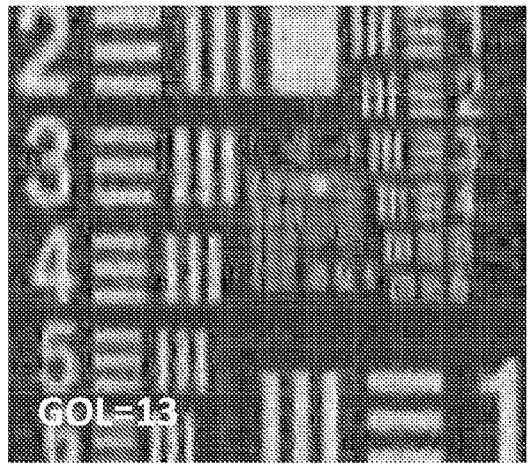
Figure 17E:
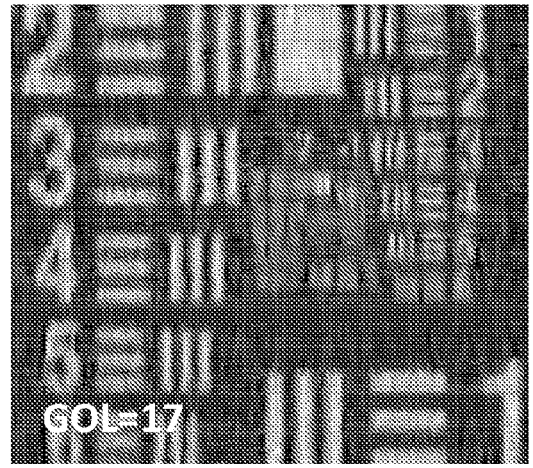
Figure 17F:
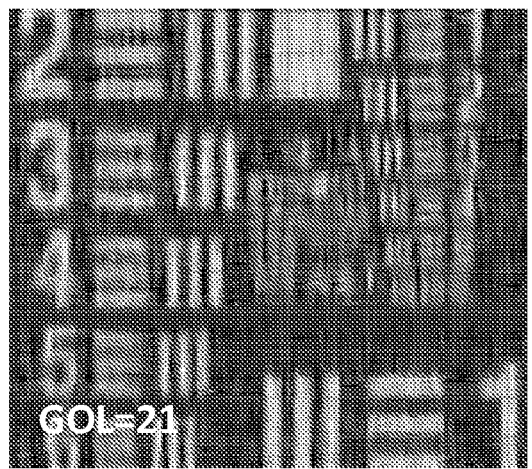

FIG. 16 is an x-y plot of image quality as a function of GOL for a 16:1 compression ratio for an image resolution of 512×512 pixels in clear water. As shown in FIG. 16, as GOL is increased, the quality is initially improved but subsequently plateaus. This is shown in FIGS. 17A-17F, which show the resulting images for GOL=3, 5, 9, 13, 27, and 21, respectively.

B4) Continued Refinement of the Reconstructed Line

One aspect that of the various embodiments that is different from most other DCS work (such as sensor network applications) is that since the illuminator has limited aperture, each line can be solved within multiple groups as the vehicle moves through the target scene. As such, the solution of a particular line L can be continuously refined by buffering all solutions to line L and determining the optimum choice as the final solution. There are several different approaches that can achieve this, two listed below are: a) Comparing the sparsity of the common components of each solution—the solution that the common component with less sparsity should render better results since this is evidence that the joint sparsity was better exploited; and b) Applying filtering (i.e., median filter) among all solutions for each pixel k of line L:

$$I_{final}(k,L) = \text{median}((I_s(k,L)), s=1 \ldots 2B$$

where $I_s(k,L)$ are the solution from the different group s.

Figure 18:
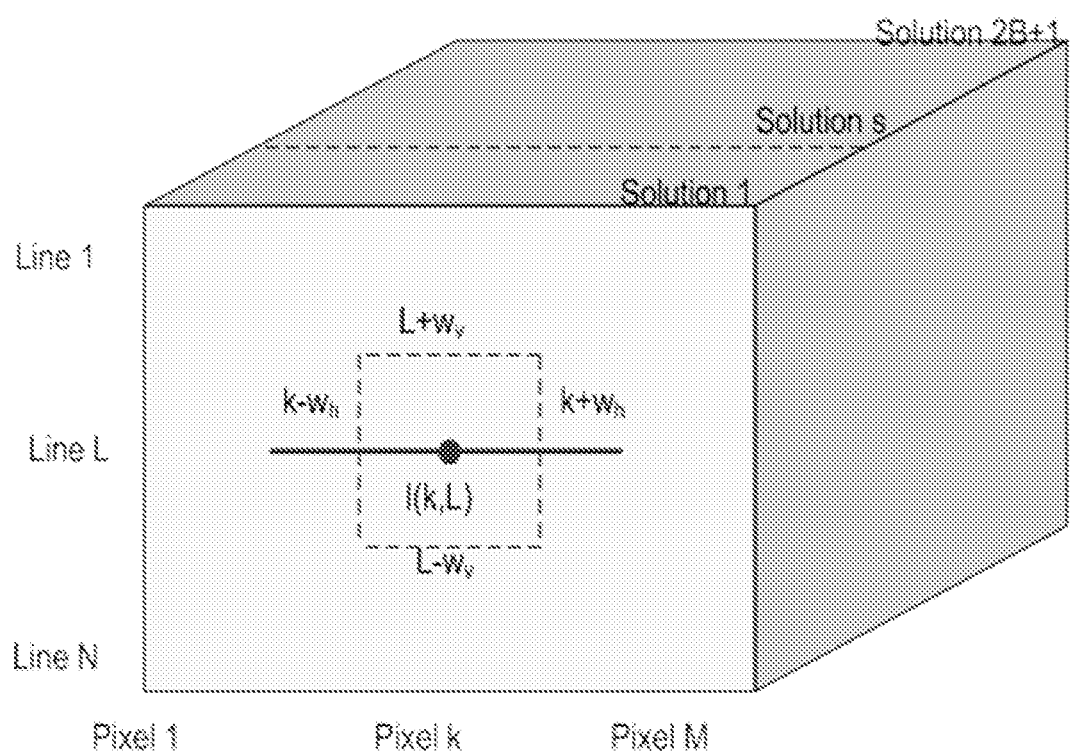
FIG. 18 schematically illustrates the optimizing or filtering that results from using the different solutions of the correlated spatial neighborhood surrounding pixel (k,L) according to the invention.

More sophisticated spatial filters that attempts to reach an jointly optimize result utilizing not only all the solutions of pixel k of line L, but also to take advantage of the highly correlated nature of its spatial can be also more advantageous at the expense of more processing complexity:

$$I_{final}(k,L) = \text{optimize}(I_s(k+k_r, L+L_r)), s=1 \ldots 2B,$$
$$k_r = -w_h \ldots w_h, L_r = -w_v \ldots w_v$$

where $w_h$ is the horizontal processing window and $w_v$ is the vertical processing window. This is schematically illustrated in FIG. 18 which shows the optimizing or filtering that results from using the different solutions of the correlated spatial neighborhood surrounding pixel (k,L). One exemplar implementation of such filtering could be the bilateral filtering with a 3D kernel.

B5) Mitigating Scattering in Underwater Environment

Figure 19:
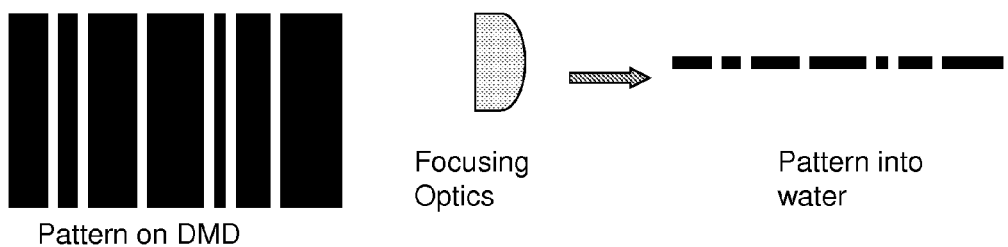
FIG. 19 schematically illustrates the use of focusing optics to convert a DMD 2D pattern to 1D measurement pattern according to the invention.
Figure 20:
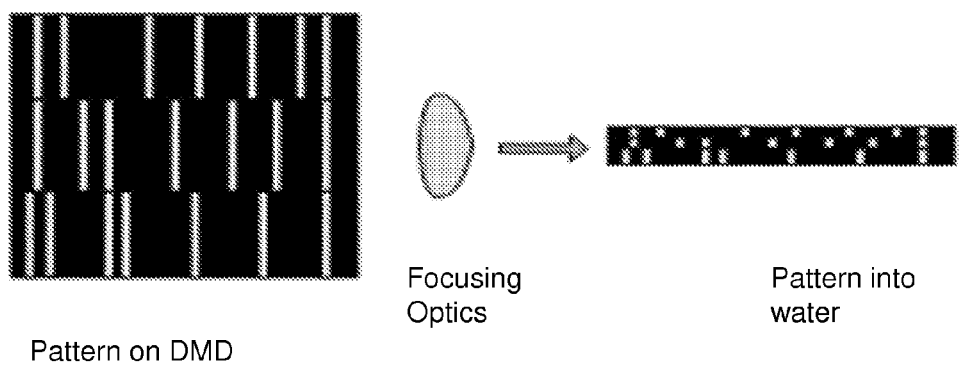
FIG. 20 schematically illustrates the use of focusing optics to convert DMD 2D pattern to multi-bands of 1D measurement pattern according to the invention.

To measure and reconstruct each individual line in the underwater environment, the detrimental effect of volume scattering on CS measurement matrices design and signal reconstruction discussed in Ouyang et al. are still a concern in the line based implementation. Therefore these concepts and approaches are still valid for use with the various embodiments. As noted above, a DMD will modulate the laser source to illuminate the entire line with a series of random patterns to spatially modulate the current target line and generate CS measurements. One difference from the implementation discussed in Ouyang et al. is that such a pattern will be focused in one direction to make it cover one line on the target plane with greater radiant intensity, as shown in FIG. 19. FIG. 19 schematically illustrates the use of focusing optics to convert a DMD 2D pattern to 1D measurement pattern. In some embodiments, more sophisticated projection optics can allow the DMD be partitioned in one dimension (i.e., vertically) into multiple different bands while retain the high resolution in the other dimension (i.e., horizontally), as shown in FIG. 20. FIG. 20 schematically illustrates the use of focusing optics to convert DMD 2D pattern to multi-bands of 1D measurement pattern. By turning on the patterns in the appropriate band, such an implementation can help to compensate for illumination shifting due to fast platform movement.

A receiver consisting of an array of sensitive narrow field of view (FOV) photo-detection elements will record target reflection, and as it is known to improve contrast for underwater Lidar applications, electronic gating can also be used to reduce volume backscattering. Alternatively, two adjacent measurement matrices consisting of the same pattern with flipped polarity can be used, where the difference of the two corresponding measurements will be used as one input stream for the image reconstruction process. However, additionally, a radiative transfer model can be used to predict the actual measurement patterns on the target line. Moreover, the difference between the two adjacent patterns can be used as another input stream for the image reconstruction process. Such architecture simplifies the hardware design and makes it possible to develop a compact and robust extended range underwater imaging Lidar system. B6) Comparison to Frame-based CS imaging.

Figures 21A, 21B:
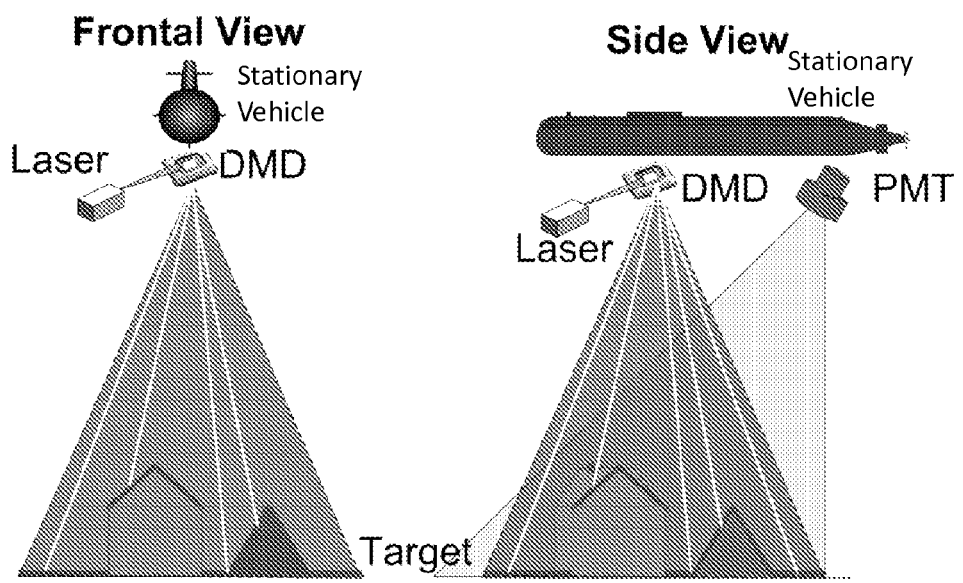
FIGS. 21A-21C schematically illustrates a frame based CS imager system.
Figure 21C:
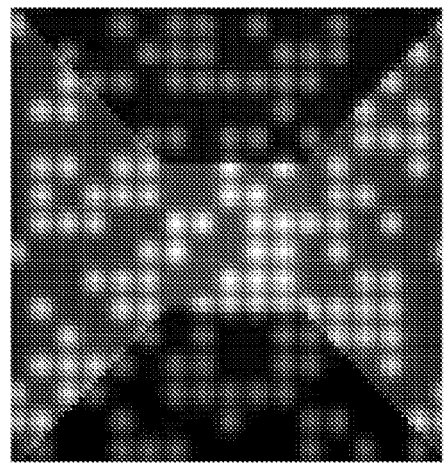
Figure 22C:
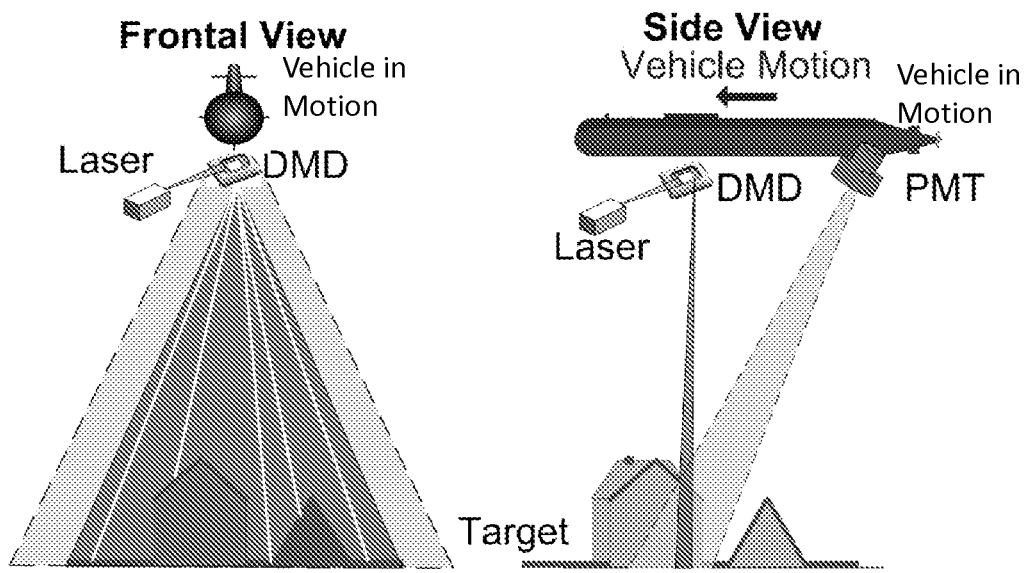
Figure 22C:
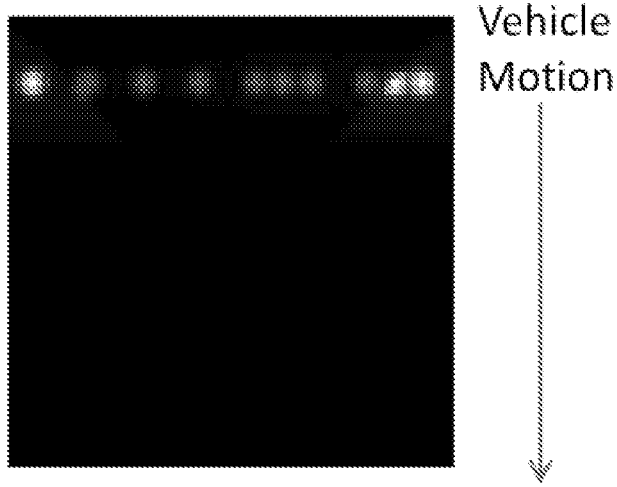

FIGS. 21A-21C and FIGS. 22A-22C illustrate the differences between frame based CS imager systems and compressive line sensing systems. As shown in FIGS. 21A and 21B, the imaging is performed by providing a stationary or hovering vehicle and illuminating and sensing a target area consisting of a frame (i.e., a 2D region). The sensing pattern for such a target area is shown in FIG. 21C. In contrast, as shown in FIGS. 22A and 22B, the imaging can be performed by a vehicle or other platform moving over the target area, but illuminating only a line or substantially 1D region of the target area. As used herein, the terms "line", "slice", "stripe", "1D region", an "substantially 1D region" refer to regions in which the width of the region (perpendicular to the direction of motion of the platform) is greater that the length (parallel to the direction of motion of the platform) of the region. The sensing pattern for such a sensing is shown in FIG. 21C. Therefore, while the basic hardware may be similar, there are two differences, as shown in Table 1:

TABLE 1

Comparison of Frame-based CS imaging and Compressive line sensing imaging

| | Frame based CS imager | Compressive line sensing imager |
|---|---|---|
| Platform motion | Hold stationary during whole sensing process | Moving through the target region in linear motion |
| Laser and receiver apertures | Cover whole target scene | Laser aperture is narrow along-track to cover only a line segment and wide cross-track to cover the |

TABLE 1-continued

Comparison of Frame-based CS imaging and Compressive line sensing imaging

| Frame based CS imager | Compressive line sensing imager |
|---|---|
| | whole width of the line; (i.e., patterned fan beam FIGS. 22A and 22B). Less ambient light will be collected with the narrow along-track aperture but cross-track angular aperture needs to ensure the patterned laser fan beam is within its field of view. |

B6) Compressive Line Sensing Process Flow

Based on the above analysis, the CLSUI system design is summarized. The three components developed for the frame based system: model predicted reconstruction; multi-scaled measurement matrices and polarity flipping to construct bipolar measurements/matrices, will be retained with the difference that 1D patterns will be generated by the SLM device. The illuminator of the CLSUI system shares some similarity with the Streak Tube Imaging Lidar (STIL) system which deploys a 1-D fan beam (wide cross-track, narrow along track beam divergences) type illumination. However, the significant difference is that instead of flashing the target line with uniform light as in STIL, in the illumination scheme for a CS based system, a line of "patterns" generated via SLM is used to "encode" the current target line. During the system operation, the number of measurements per line will firstly be computed from the given expected platform speed and the SLM refresh rate. The line group count gnum—the number of lines to be solved jointly, will be determined according to the system and environment condition such as the water turbidity, target distance, laser divergence etc. Nevertheless, adjusting this parameter during the operation after certain image quality evaluation is trivial. After the sensing of one line is accomplished, a first-in-first-out (FIFO) that consists of gnum sets of measurements and measurement matrices will be update with the new data. Subsequently, the group of lines in the FIFO will be solved via solvers for DCS JSM-1 model and/or GDCS model. The resulting solutions for each line will be buffered as well. When a line moves out of the effective vertical aperture, one of the two methods outlined in section B4 can be adopted to obtain the final solution.

The key concepts of the frame based CS imager design outlined in Ouyang et al. will again be adopted in the measurement and reconstruction in the compressive line sensing implementation. These concepts are summarized below:

Multi-scale Measurement Matrix Design: The dither pattern is divided into small blocks of pre-defined size. Only one "on" pixel will be present within each block and the location of this pixel within the block $\{b_i\}$ will be generated from a pseudo-random sequence $\{p_{1i}\}$. The polarity of each block will be determined by a second pseudo random sequence $\{p_2\}$. The overall dither pattern will be the product of $\{p_2\}$ and $\{p_{1i}\}$:

$$\begin{cases} x(i, k) = 1, & \text{iff } p_{1i}(k) * p_2(i) = 1 \\ x(i, k) = 0, & \text{otherwise} \end{cases}$$

where x is the pixel intensity, i are the block indices, and k is the pixel location within a block.

Model Assisted Image Reconstruction: An equally important aspect of any CS application is the optimization process to reconstruct the image. The process of spatially modulating the target with an incoming binary dither pattern $\{A_b\}$ can be modeled as:

$$y_m = \sum [((A_b \otimes BSF_{IT})X) \otimes BSF_{TR} + \xi(0, \sigma)]$$
$$= \sum [(A_{PSF}X) \otimes BSF_{TR} + \xi(0, \sigma)]$$

where $BSF_{IT}$ and $BSF_{TR}$ are the Beam Spread Functions from illuminator to the target and from target to the receiver respectively. As can be seen in (2), instead of $\{A_b\}$, the target X is actually modulated with $\{A_{BSF}\} = \{A_b \otimes BSF_{IT}\}$. Therefore $\{A_{BSF}\}$ will be used as the measurement matrices in image reconstruction. A radiative transfer model can be used to predict the beam spread function measurement pattern on the target plane with given inherent optical properties (IOPs) and system parameters. The beam spread function can be further adaptively enhanced in a semi-blind mode (i.e., using the radiative transfer model predicted BSF as initial input and iteratively enhance the BSF while reconstructing the image).

Figure 23:
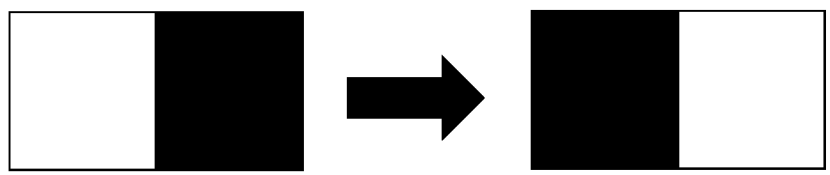
FIG. 23 schematically illustrates a polarity flipping technique according to the invention.

Polarity flipping binary signal generation: When imaging a static scene, the scene geometry and incident laser power will remain unchanged between measurements. Consequently, the backscatter can be modeled as a Gaussian noise with a constant mean. To reduce backscatter, a polarity flipping technique can be used, as schematically illustrated in FIG. 23. Each dither pattern is loaded twice, first with mirror "on" corresponds to a digital "1" in $\{p_2\}$, and then with mirror "off" corresponds to a digital "1". The difference of the two readings reduces the backscattering to a zero-mean Gaussian:

$$y_m = y_{m+} - y_{m-}$$
$$= \sum [A_+ X + \xi(C, \sigma))] - \sum [A_- X + \xi(C, \sigma))]$$
$$= \sum [(A_+ - A_-)X + \xi(0, \sigma)]$$

This potential backscattering reduction is unique to CS based imaging system.

Figure 24:
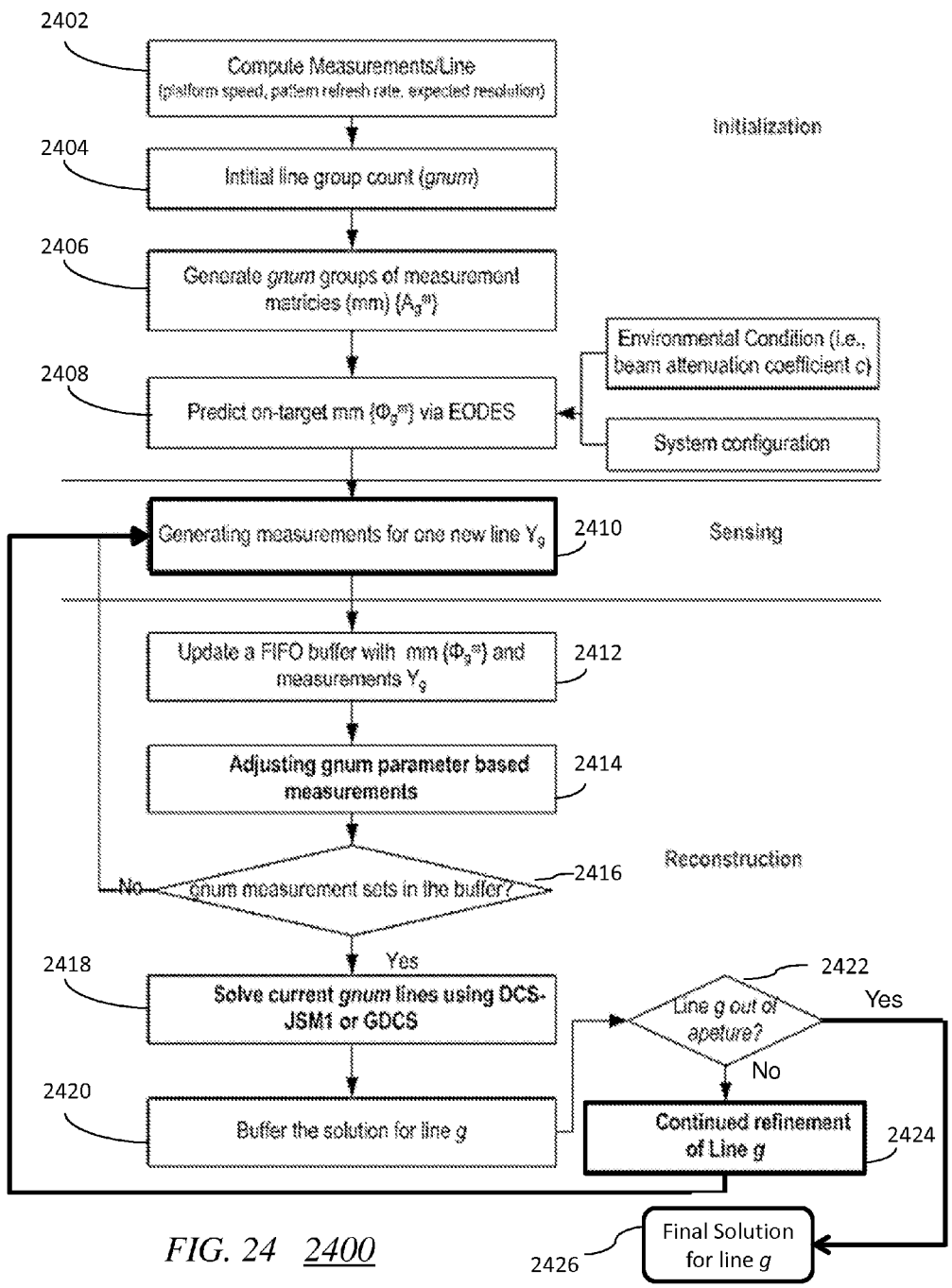
FIG. 24 is a flow chart of an exemplary method 2400 for performing compressive line sensing according to the invention.

FIG. 24 is a flow chart of an exemplary method 2400 for performing compressive line sensing in accordance with the various embodiments based on the various concepts described above. The method begins with an initialization phase (steps 2402-2408). At step 2402, the number of necessary measurements per line is computed. The measurements per line can be based on various parameters associated with the acquisition of the image. These can parameters can include the platform or vehicle speed, the refresh rate required, and the resolution needed or expected.

The method then proceeds to step 2404. At step 2404, the number of measurement lines (gnum) that will be solved together is selected, i.e., the aperture for the compressive line sensing of the various embodiments. This number can also be based on various parameters, including, but not limited to, the environmental conditions at which the measurements will be taken, Such conditions can include a turbidity of the medium (e.g., the water), types of particles contributing to the turbidity, and any other factors that can affect the propagation and scattering of the light through the medium.

Once gnum is determined at step 2404, gnum groups of measurement matrices (mm) can be generated at step 2406. Thereafter the on-target measurement matrices can be predicted using a radiative transfer model at step 2408, based on environmental conditions and the configuration of the system. The predicted measurement matrices can then be used in the model assisted image reconstruction (step 2418). In some embodiments, the EODES electro-optical system model can be used. However, the various embodiments are not limited in this regard and other radiative transfer models can be used.

After the necessary measurement matrices are generated at steps 2406 and 2406, sensing and reconstruction phases can begin. At step 2410, measurements for one new line (Yg) are obtained to provide the sensing phase. The number of measurements for line g are based on the number obtained at step 2402.

The reconstruction phase then begins at step 2412. After the sensing of one line is accomplished, a first-in-first-out (FIFO) that consists of gnum sets of measurements and measurement matrices will be updated at step 2412 with the new data. The gnum parameter based measurements can then be adjusted at step 2414. This can be performed in accordance with the methods described above with respect to B3. Thereafter, at step 2416, the data is evaluated to determine whether the buffer is full. That is, determining whether measurements for gnum lines been obtained. If less than gnum lines have been obtained, steps 2410-2414 are repeated until the buffer is full, i.e., gnum lines are obtained.

Once gnum lines are obtained, the group of lines in the FIFO are solved at step 241 to obtain a solution for all lines. For example, the group of lines can be solved via solvers for DCS JSM-1 model and/or GDCS model. The resulting solutions for each line are then buffered at step 2420.

Figure 25:
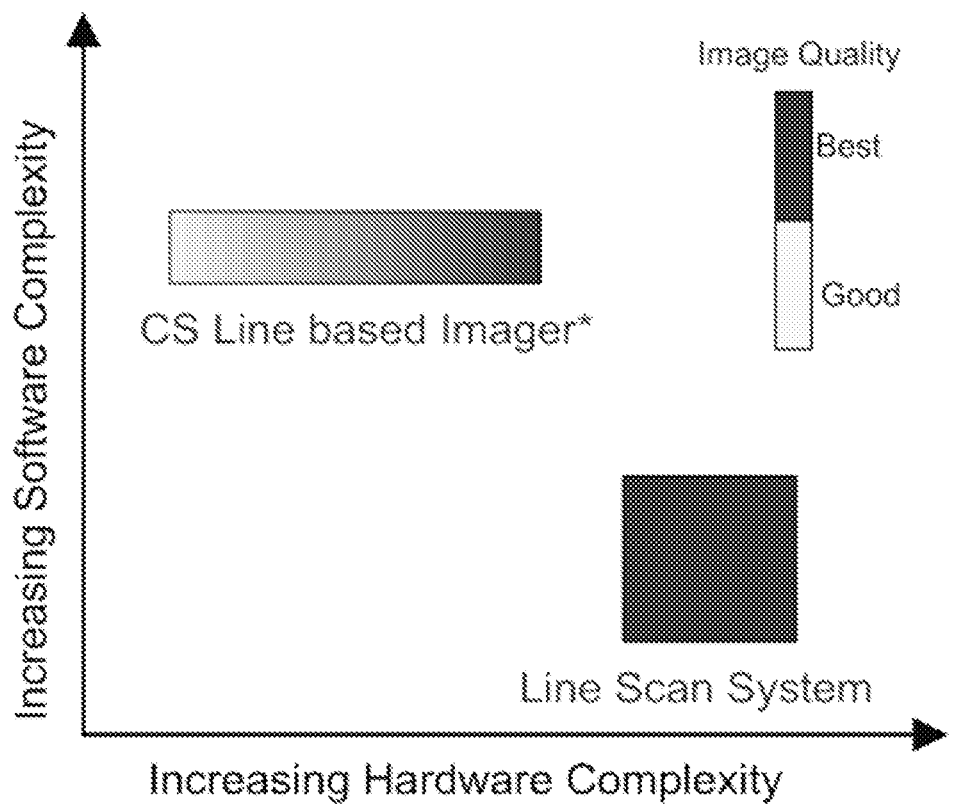
FIG. 25 schematically illustrates the tradeoff between hardware and software complexity for CS imaging systems versus line scan systems.

At step 2422, it is then determined whether or not a line has moved outside of the aperture. If a line is still in the aperture, further refinement is required at step 2424, namely repeating steps 2410-2420. When a line moves out of the effective vertical aperture the method can proceed to step 2426 to obtain a final solution for that line. In some embodiments, one of the two methods outlined in B4) can be utilized to obtain the final solution. The method 2400 can then be repeated for the remainder of the lines being measured, B7) Advantages of the CS Imaging System Design Most of the traditional underwater electro-optical systems such as LLS are more hardware-oriented solutions: system enhancements in general place the premium on the development of new hardware. Relying on the highly adaptive solid-state SLM devices, the CS based technique provides a more software/algorithmic oriented approach, therefore can be more adaptive to the changing environment and/or task requirements. The system innovation/enhancement can be less capital intensive, albeit any hardware upgrade can certainly improve system performance as well. This is illustrated with respect to FIG. 25.

The achievable image resolution of the CS based design is impacted by the laser spreading along the path from the illuminator to the target while the propagation from the target to the receiver is essentially diffuse attenuation on the total photon flux for all the measurements. For the LLS systems, the resolution is influenced by both the laser divergence and the receiver aperture. While fully realizing the advantage of the CS based design requires arduous effort to improve the design of the measurement matrices and the solvers as well as to mitigate other environmental and system interferences, this certainly is one of factors motivating the continued investigation of this technique. Another related interesting observation is that the effect of the scattering on the intensity image can be regarded as lowpass filtering the target scene with the passband shrinking with the increased water turbidity. Alternatively, this can also be stated that the signal will be more sparse with the increased water turbidity—desirable for the CS applications (albeit the measurement will be more noisy).

In addition, the described CS based imager design uses a wide-aperture receiver and does not require direct line-of-sight between the target plane and receiver in turbid water—one of the major motivations for adopting an illuminator based SLM over a receiver based approach. In the distributed imaging and communication arrangement, where the illuminators and receivers are on different platforms, the integration of these two attributes is highly desirable.

The described CS imaging system provides the potential of achieving desirable image resolution without requiring high repetition rate (i.e. costly) laser. In addition such "compressing during sampling" paradigm requires lower speed and narrower bandwidth electronics, which in turn improves system noise performance and reduces production costs. The CS imager maintains good photon efficiency via using the "bucket" photon collector such as a PMT, like the LLS system except with a much wider instantaneous FOV.

Replacing the bulky scanning mechanical and optical components used in the conventional LLS with the commercially available solid-state SLM device such as a DMD helps to improve the system reliability and compactness. On the other hand, the laser and PMT developed for conventional LLS can be readily used in a CS based imager. Additionally, effective volume backscatter reduction techniques developed for the LLS system, such as the pulsed laser and range-gated receiver and the modulated pulsed laser/receiver, remain applicable to the CS based imaging system.

B8) Image Reconstruction Performance Demonstration

Figure 26A:
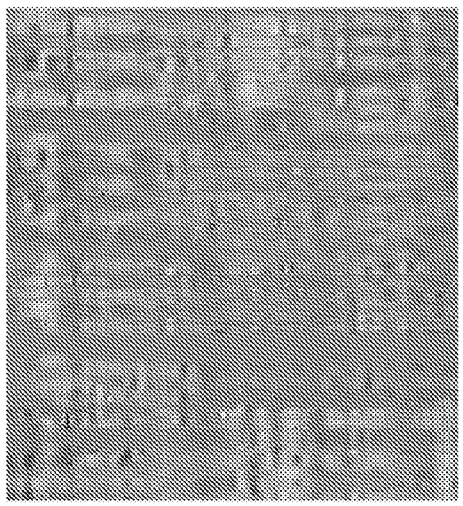
FIGS. 26A-26D show results of image reconstruction performance for compressive line sensing with each line decoded independently (FIG. 26A) and jointly (FIGS. 26B-26D) according to the invention.
Figure 26B:
Figure 26C:
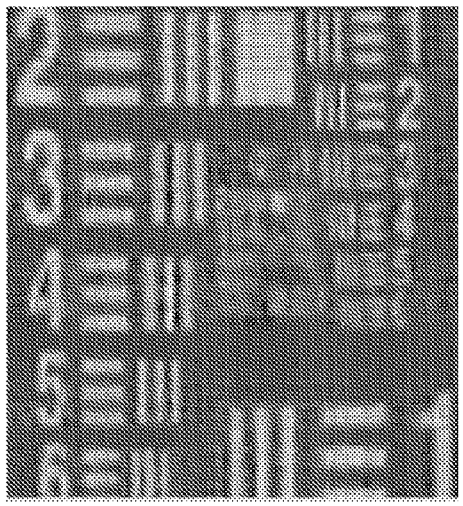
Figure 26D:
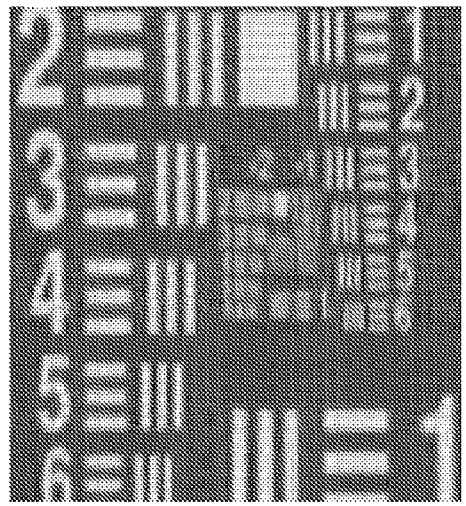

The simulation results in FIGS. 26A-26D compare the image reconstruction performance for compressive line sensing with each line decoded independently (FIG. 26A) and jointly (FIGS. 26B-26D). All images are at 512×512 resolution, using Cohen-Daubechies-Feauveau (CDF) 9/7 wavelet as sparsifying basis; Clearwater (c=0.04), no receiver noise. In particular, FIG. 26A shows the results for independent decoding and, 64 measurements/line, i.e., a 8:1 compression. FIG. 26B shows the results for joint decoding using 17 lines/group and 16 measurements/line, i.e., a 8:1 compression. FIG. 26C shows the results for joint decoding using 7 lines/group and 32 measurements/line, i.e., a 16:1 compression. FIG. 26D shows the results for joint decoding using 7 lines/group and 64 measurements/line, i.e., a 8:1 compression. As can be observed from these results, the joint decoding provides superior performance with a significantly few number of measurements required per line.

Figure 27:
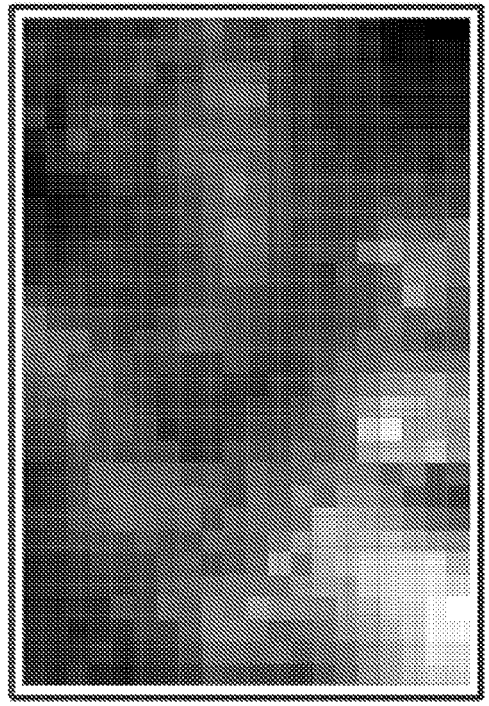
FIG. 27 shows the results for recovering image content from relatively noisy data according to the invention.
Figure 27:
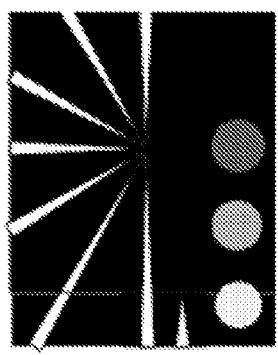
Figure 27:
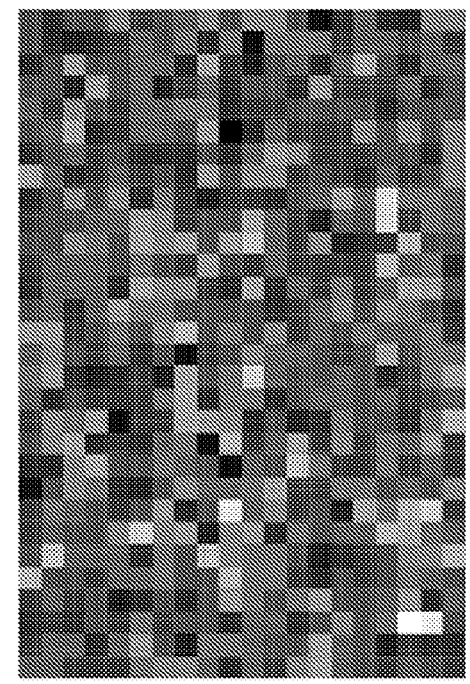

The paradigm of using radiative transfer model not just as a prediction tool but as a component in image reconstruction/enhancement technique can also used to enhance the pulse gated underwater laser imaging system. Through first applying a bilateral filter based pulse shaping using the pulses in the adjacent correlated spatial neighbor, then with given environmental and system conditions, the beam spread function (BSF) predicted from the radiative transfer model is used to reverse the lowpass filtering effect of the water medium to enhance the image resolution, significant image quality improvement can be achieved. The image noise performance can be further improved by adopting a receiver with multiple photomultiplier tubes (PMT) with overlapping FOV, where the initial beam spread function for each PMT can be predicted via the radiative transfer model; the initial channel weight can be determined from the noise floor of each channel to implement a multi-channel deconvolution (MCD) framework. This is illustrated in FIG. 27, which shows that some image content can be recovered from relatively noisy data.

While exemplary embodiments of the invention have been described, the invention is not so limited. Numerous modifications, changes, variations, substitutions and equivalents will be apparent to those skilled in the art without departing from the spirit and scope of the present invention as described in the claims. It is also noted that, to more clearly present features pertinent to the invention, numerous components have been expressly illustrated while other components may not have been illustrated. Further, in order to illustrate features of the invention, components and features illustrated in the figures may not be to scale. Accordingly, the invention is only limited by the claims which follow.

What is claimed is:

1. A method, comprising:
   obtaining data associated with a plurality of return optical signals generated for a series of substantially one-dimensional (1D) regions of a target area, each of the plurality of return optical signals generated by illuminating each of the series of 1D regions using a substantially 1D pattern if light along a width of the 1D regions;
   identifying at least one aperture section for the target area that includes at least a portion of the 1D regions to yield aperture 1D regions for each at least one aperture section;
   for each at least one aperture section, computing solutions for the aperture 1D regions using a distributed compressive sensing (DCS) technique;
   for each of the 1D regions, combining the solutions from each at least one aperture section to produce the sensor information for each of the 1D regions.

2. The method of claim 1, wherein the obtaining for comprises:
   receiving measurement data corresponding to the return optical signals for each of the 1D regions; and
   assembling a measurement matrices for each of the 1D regions based at least on the measurement data.

3. The method of claim 2, wherein the measurement matrices are based on a model accounting for at least environmental conditions during collection of the measurement data and a configuration of a transmitter assembly for providing the illumination and the receiver assembly for the collecting of the return optical signals.

4. The method of claim 1, wherein the obtaining further comprises directing light from a light source on a platform to the series of 1D regions using a microdisplay device at the platform to generate the return optical signals and collecting the return optical signals using a receiver at the platform, wherein the microdisplay device comprises a plurality of controllable elements, and wherein the directing comprises adjusting the plurality of controllable elements to cause the light to be reflected towards each of the series of 1D regions as the 1D pattern of light.

5. The method of claim 4, wherein the obtaining further comprises collecting one or more sets of measurement data for each of the series of 1D regions, wherein a number of the sets of measurement data for each of the series of 1D regions is selected based on at least one of a speed of the platform, a desired refresh rate for the sensor information, and an expected resolution of the sensor information.

6. The method of claim 1, wherein the computing is performed using one of a DCS-JSM1 algorithm or a GDCS algorithm.

7. A method for operating a sensing system on a moving platform that comprises a transmitter assembly for transmitting an optical beam transmission path to provide illumination of each of a series of adjacent substantially one-dimensional (1D) regions of a target area using substantially 1D patterns of light and a receiver assembly for defining a return optical signal transmission path from the series of 1D regions and collecting return optical signals from the series of 1D regions, the method comprising:
  initializing the sensing system to set a first number of measurements for each of the series of 1D regions, a second number of the series of 1D regions defining an aperture section of the target area, and a configuration of measurement matrices for the series of 1D regions; and
  performing a reconstruction process to assemble an image of the target area, the reconstruction process comprising:
    generating the measurements for a one of the series of 1D regions;
    updating a first-in, first-out (FIFO) buffer with an entry comprising the measurements and the measurement matrices corresponding to the one of the series of 1D regions;
    determining whether the FIFO buffer includes a number of entries equal to the second number;
    in response to the FIFO buffer including a number of entries equal to the second number computing a solution for the series of 1D regions in the FIFO buffer using a distributed compressive sensing (DCS) technique; and
    in response to the FIFO buffer including a number of entries less that the second number repeating the process.

8. The method of claim 7, further comprising:
  detecting that a one of the series of 1D regions is no longer in the FIFO buffer; and
  combining the solution for the one of the series of 1D regions from each time the reconstruction process is performed.

9. The method of claim 7, wherein the initializing comprises calculating the first number based on at least one of the speed of the platform, a refresh rate of the 1D patterns, and an expected resolution.

10. The method of claim 7, wherein the initializing comprises calculating the second number based at least on characteristics of a medium associated with the optical beam transmission path and the return optical signal transmission path.

11. The method of claim 7, wherein the measurement matrices are generated using a radiative transfer model based on at least one of environmental conditions and a configuration of the platform.

12. The method of claim 7, wherein the reconstruction process further comprises adjusting the second number based on a difference in the data between the series of 1D regions.

13. The method of claim 7, wherein the computing of the solution comprises using one of a DCS-JSM1 algorithm or a GDCS algorithm.

14. An apparatus, comprising:
  a sensing system on a moving platform that comprises a transmitter assembly for transmitting an optical beam transmission path to provide illumination of each of a series of adjacent substantially one-dimensional (1D) regions of a target area using substantially 1D patterns of light and a receiver assembly for defining a return optical signal transmission path from the series of 1D regions and collecting return optical signals from the series of 1D regions,
  a processing system for operating the sensing system, wherein the processing system is configured for initializing the sensing system to set a first number of measurements for each of the series of 1D regions, a second number of the series of 1D regions defining an aperture section of the target area, and a configuration of measurement matrices for the series of 1D regions, and performing a reconstruction process to assemble an image of the target area,
  wherein the reconstruction process comprises generating the measurements for a one of the series of 1D regions, updating a first-in, first-out (FIFO) buffer with an entry comprising the measurements and the measurement matrices corresponding to the one of the series of 1D regions, determining whether the FIFO buffer includes a number of entries equal to the second number, in response to the FIFO buffer including a number of entries equal to the second number computing a solution for the series of 1D regions in the FIFO buffer using a distributed compressive sensing (DCS) technique, and in response to the FIFO buffer including a number of entries less that the second number repeating the process.

15. The apparatus of claim 14, wherein the processing system is further configured for detecting that a one of the series of 1D regions is no longer in the FIFO buffer, and combining the solution for the one of the series of 1D regions from each time the reconstruction process is performed.

16. The apparatus of claim 14, wherein the initializing comprises calculating the first number based on at least one of the speed of the platform, a refresh rate of the 1D patterns, and an expected resolution.

17. The apparatus of claim 14, wherein the initializing comprises calculating the second number based at least on characteristics of a medium associated with the optical beam transmission path and the return optical signal transmission path.

18. The apparatus of claim 14, wherein the measurement matrices are generated using a radiative transfer model based on at least one of environmental conditions and a configuration of the platform.

19. The apparatus of claim 14, wherein the reconstruction process further comprises adjusting the second number based on a difference in the data between the series of 1D regions.

20. The apparatus of claim 14, wherein the computing of the solution comprises using one of a DCS-JSM1 algorithm or a GDCS algorithm.

* * * * *